(12) United States Patent
Kuriyama et al.

(10) Patent No.: US 9,194,839 B2
(45) Date of Patent: Nov. 24, 2015

(54) ANALYTICAL CELL

(71) Applicant: HONDA MOTOR CO., LTD., Minato-ku, Tokyo (JP)

(72) Inventors: Nariaki Kuriyama, Wako (JP); Yoshiya Fujiwara, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 14/679,259

(22) Filed: Apr. 6, 2015

(65) Prior Publication Data
US 2015/0293050 A1    Oct. 15, 2015

(30) Foreign Application Priority Data

Apr. 9, 2014   (JP) .................................. 2014-080430

(51) Int. Cl.
*G01F 23/00*   (2006.01)
*G01N 27/404*  (2006.01)

(52) U.S. Cl.
CPC .................................... *G01N 27/404* (2013.01)

(58) Field of Classification Search
CPC ................. H01J 2237/2002; H01J 2237/206; H01J 37/20; H01J 37/26; G01N 27/404
USPC ................... 250/306, 307, 310, 311, 440.11
See application file for complete search history.

(56) References Cited

U.S. PATENT DOCUMENTS

| | | | | |
|---|---|---|---|---|
| 6,631,022 B1* | 10/2003 | Kihira | .................. | G02F 1/1506 348/E5.028 |
| 2008/0179518 A1* | 7/2008 | Creemer | ................. | H01J 37/20 250/311 |
| 2010/0276277 A1* | 11/2010 | Chey | .................... | G01N 27/416 204/242 |

FOREIGN PATENT DOCUMENTS

WO   2008/141147 A1   11/2008

OTHER PUBLICATIONS

Raymond R. Unocic et al., "In-Situ Electron Microscopy of Electrical Energy Storage Materials", Annual Merit Review, DOE Vehicle Technologies Program, Washington, DC, May 9-13, 2011 [online], 2014, Retrieved on Jan. 30, 2014 from the Internet <URL: http://www1.eere.energy.gov/vehiclesandfuels/pdfs/merit_review_2011/electrochemical_storage/es095_unocic_2011_o.pdf>.

* cited by examiner

*Primary Examiner* — Michael Maskell
(74) *Attorney, Agent, or Firm* — Carrier Blackman & Associates, P.C.; Joseph P. Carrier; William D. Blackman

(57) ABSTRACT

An analytical cell includes first and second holders. The first and second holders each contain a substrate having a through-hole and a transmission membrane with an electron beam permeability so as to cover the through-hole. The first and second holders are stacked to form an overlapping portion such that the transmission membranes face each other and that an inner space therein containing the electrolytic solution is sealed. The through-holes face each other across the transmission membranes to form an observation window. Negative and positive electrode active materials are separated from each other and contact the electrolytic solution in the observation window. A transmission body containing an electron beam permeable solid is formed between at least one of the negative and positive electrode active materials and the transmission membrane.

4 Claims, 40 Drawing Sheets

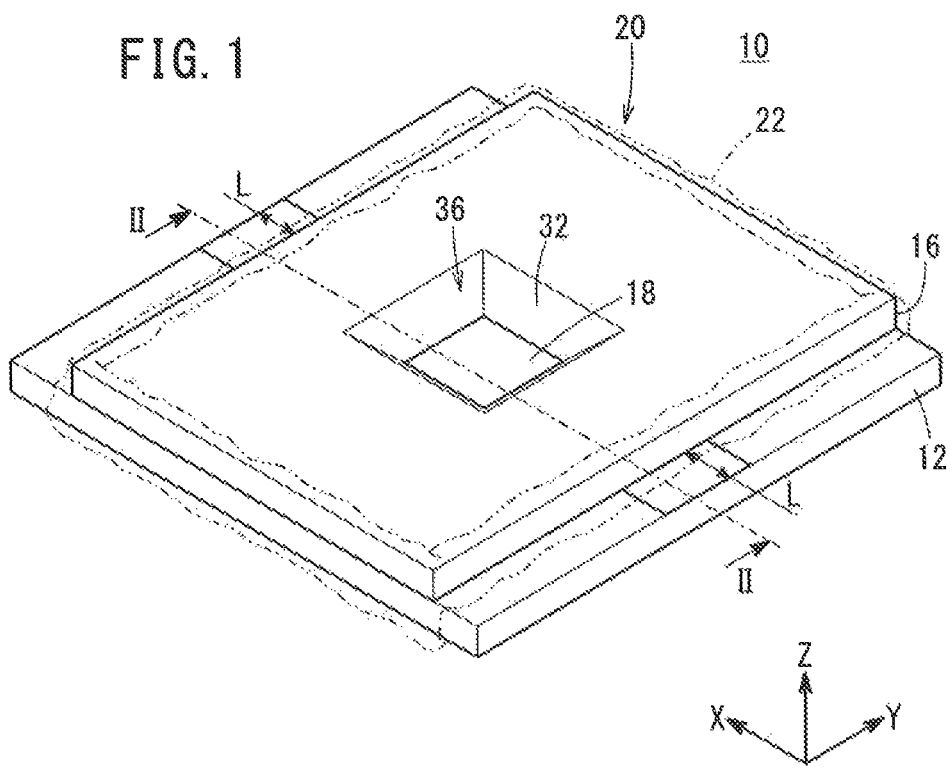

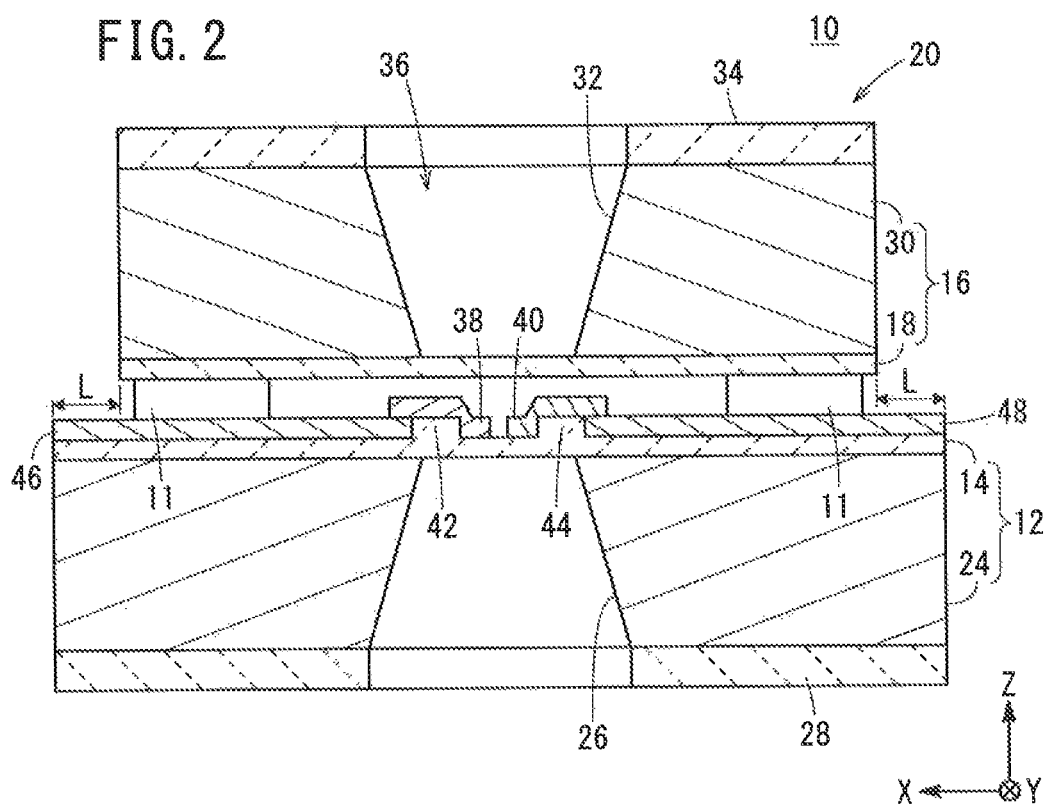

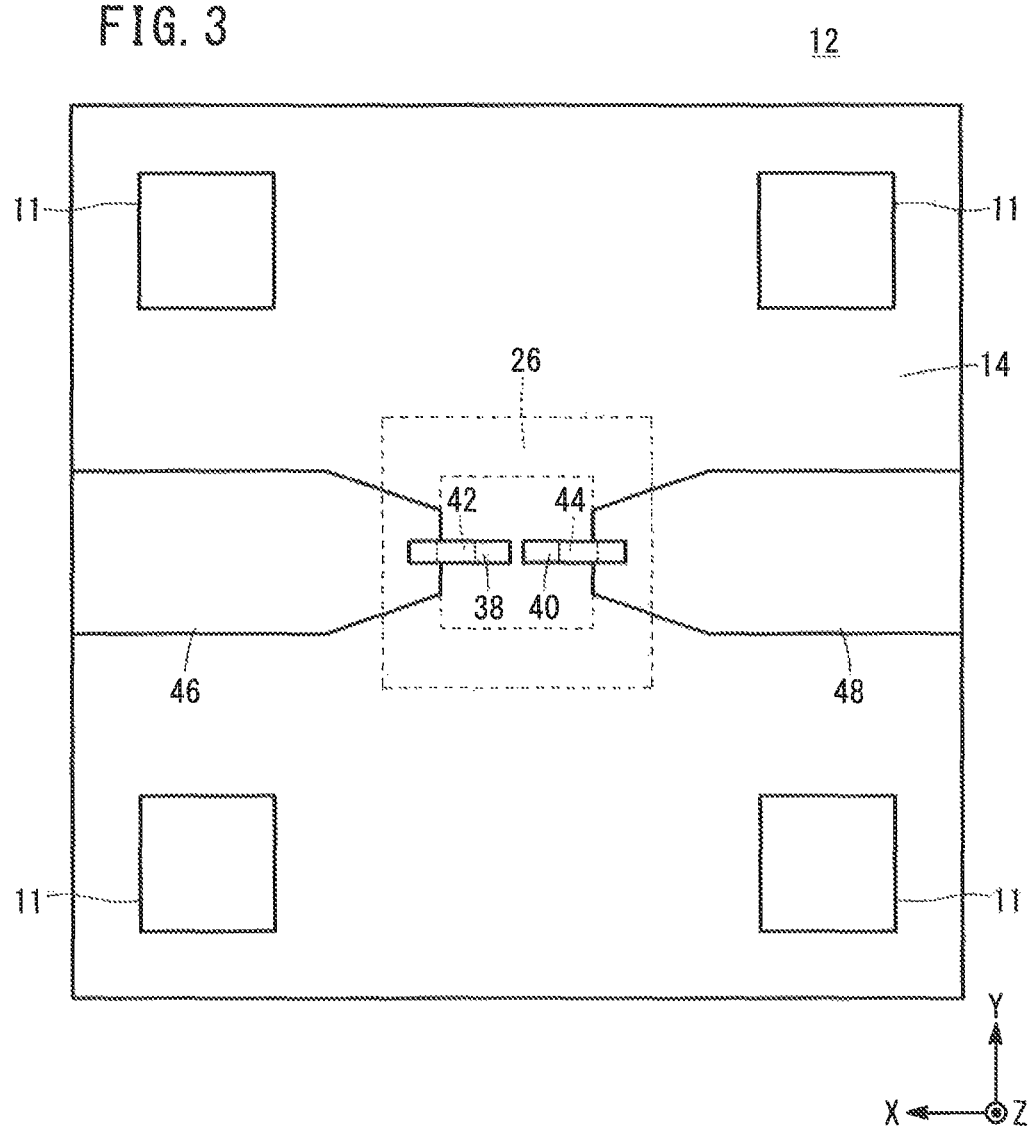

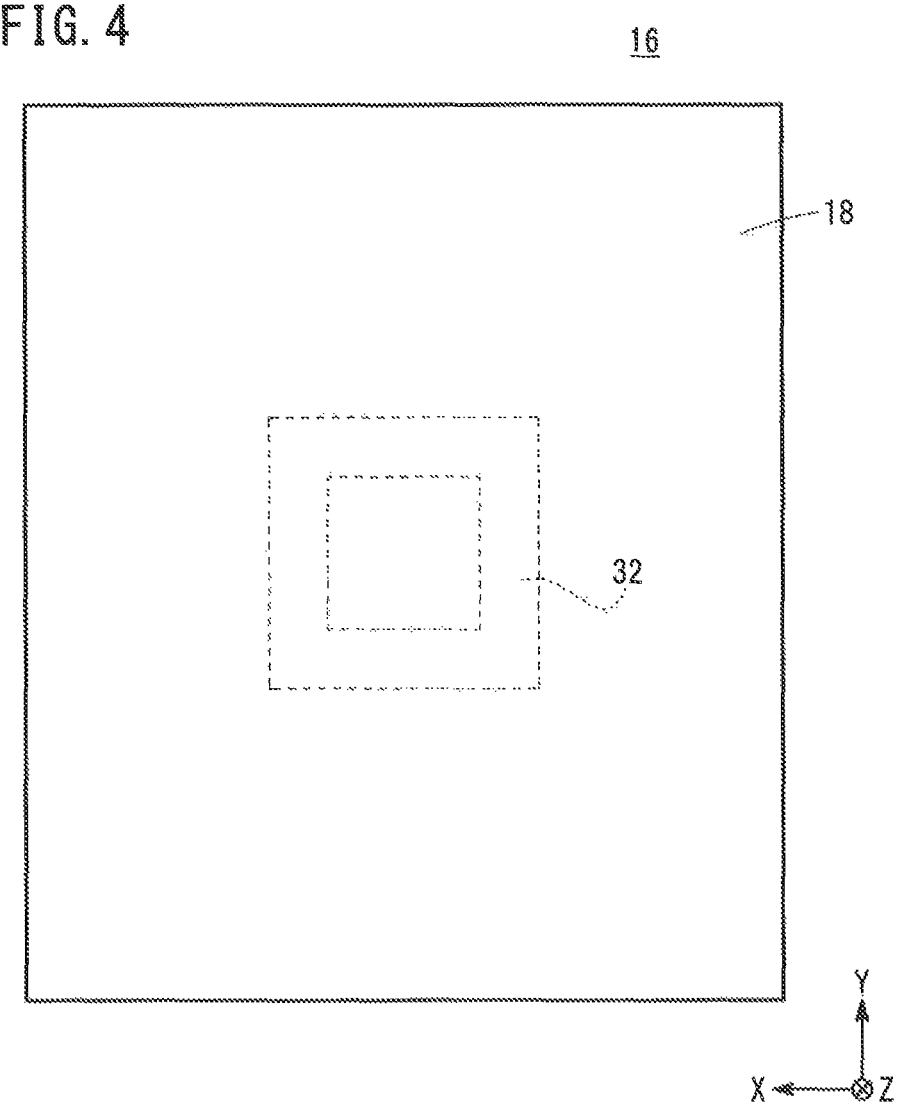

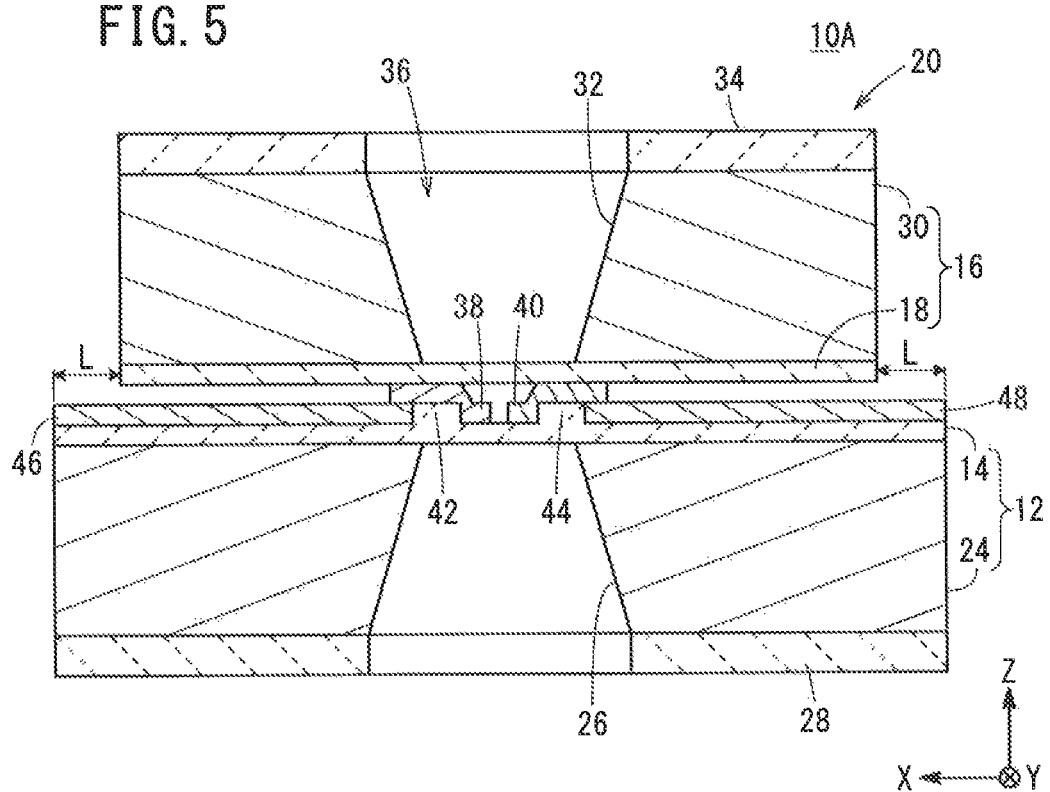

FIG. 8A
FIG. 8C
FIG. 8B
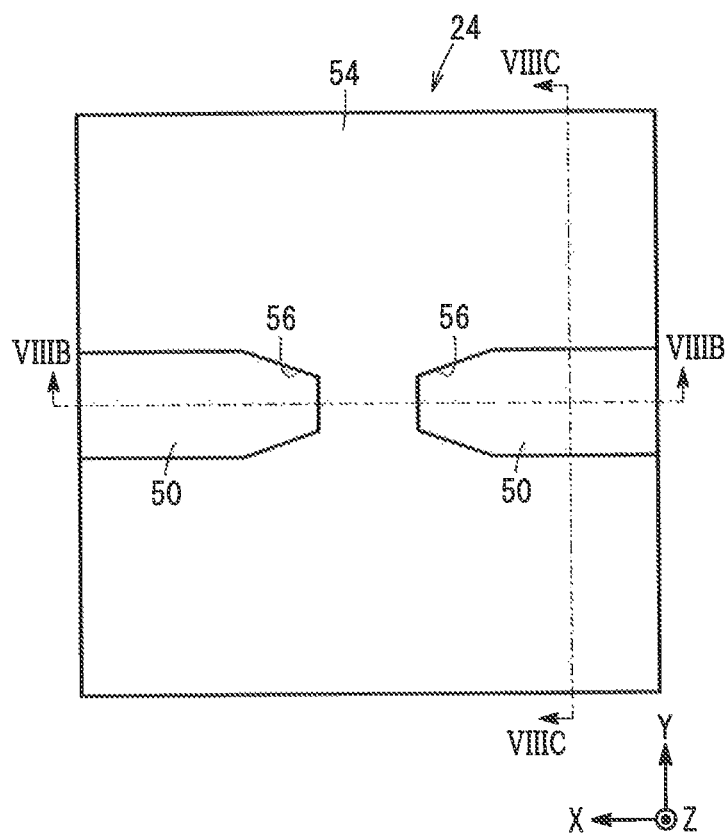
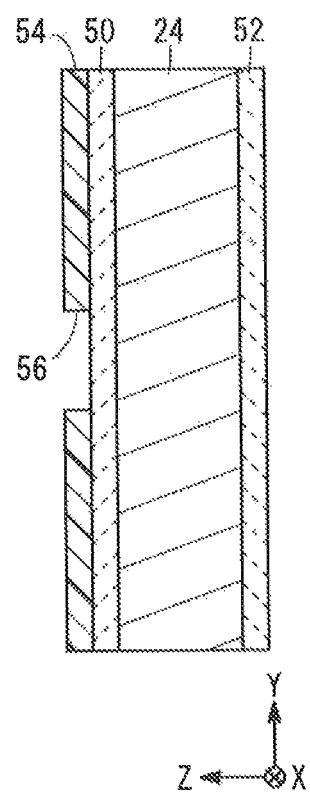
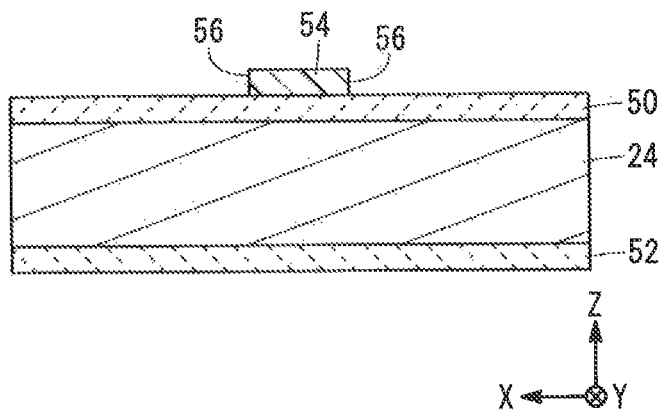

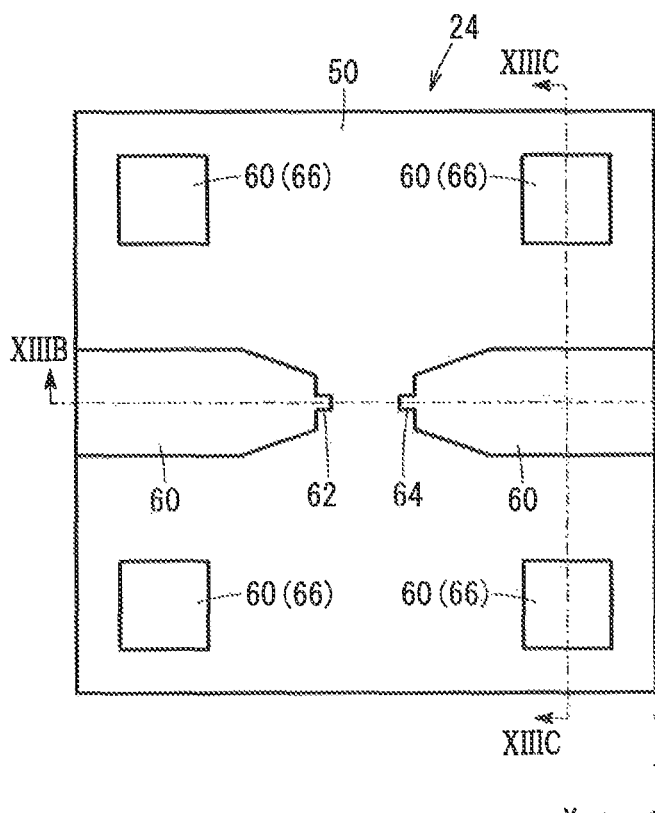
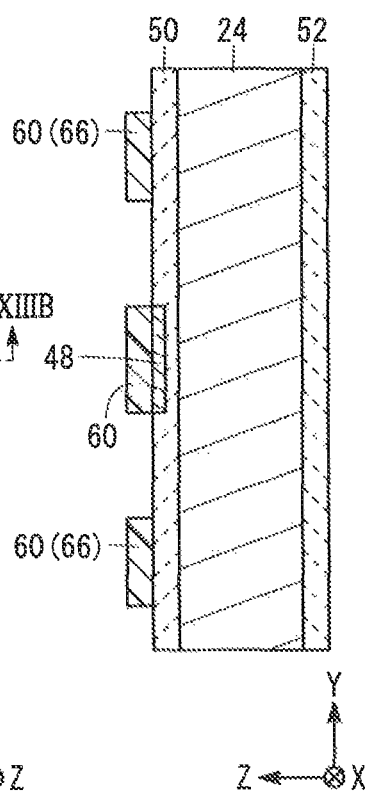
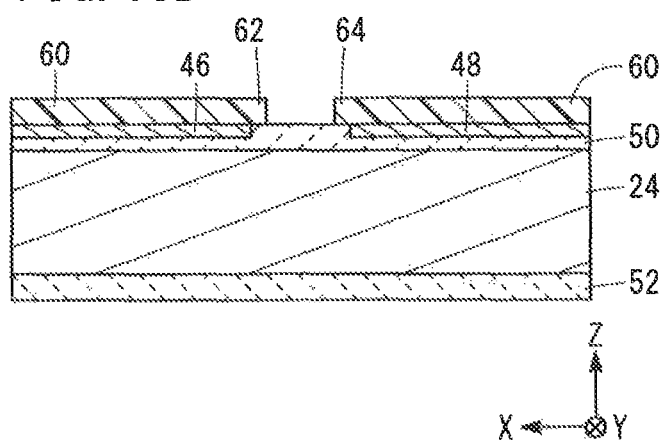

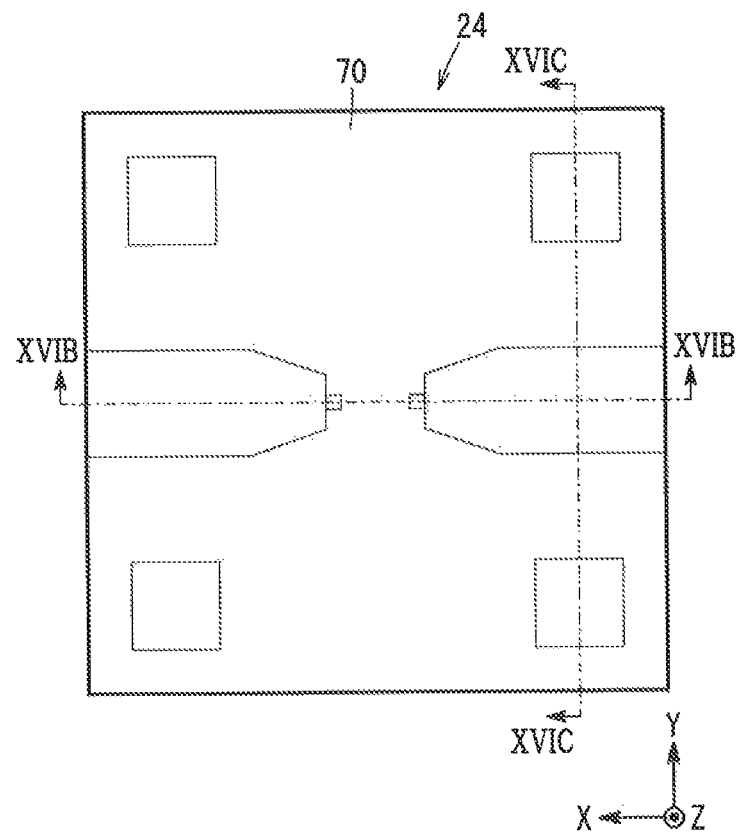
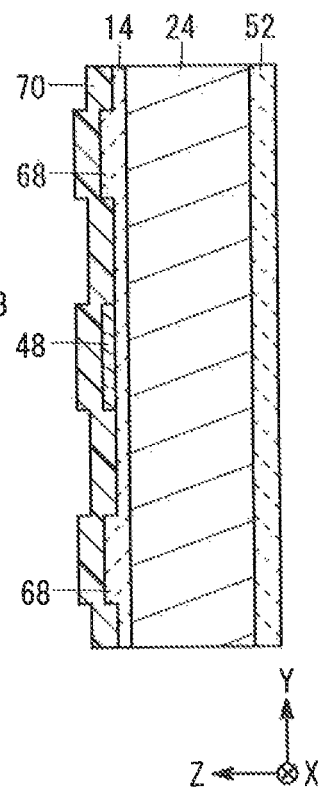
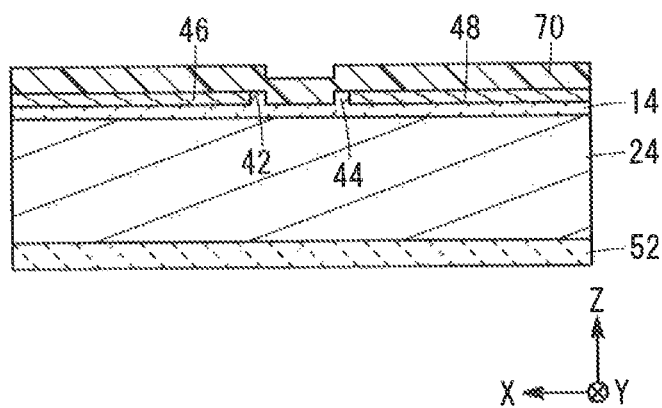

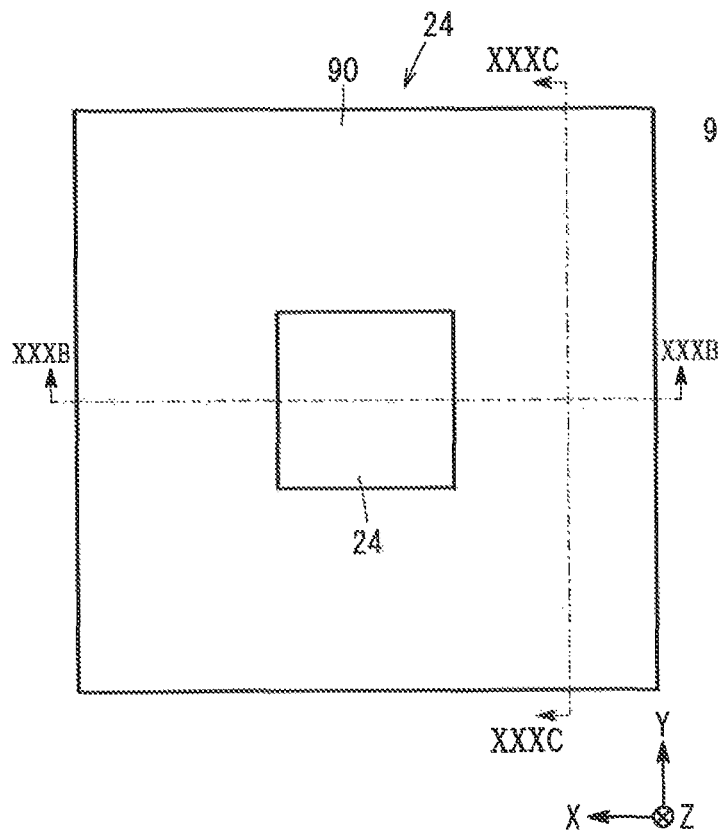
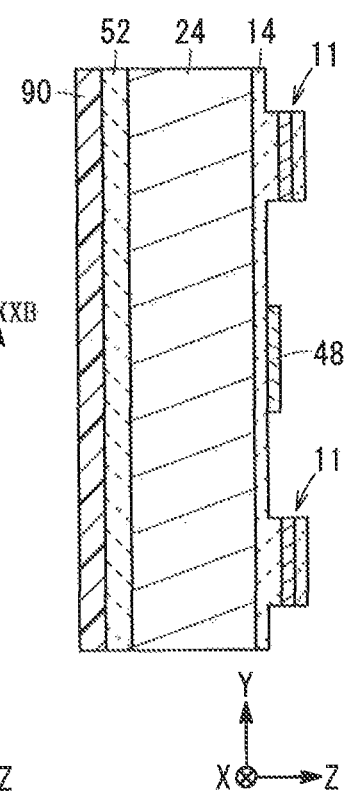
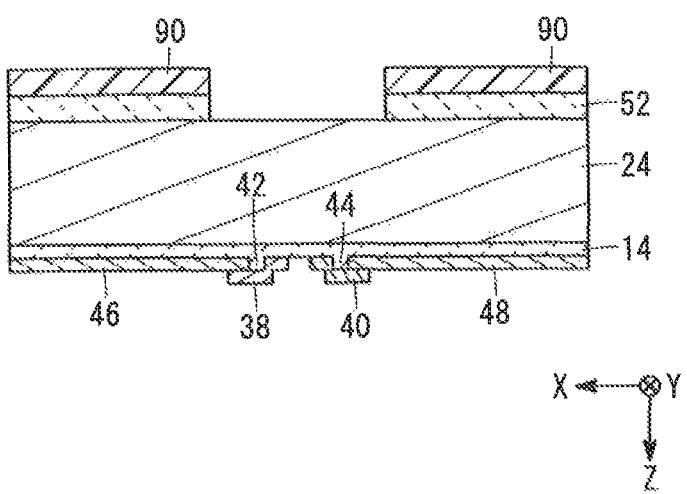

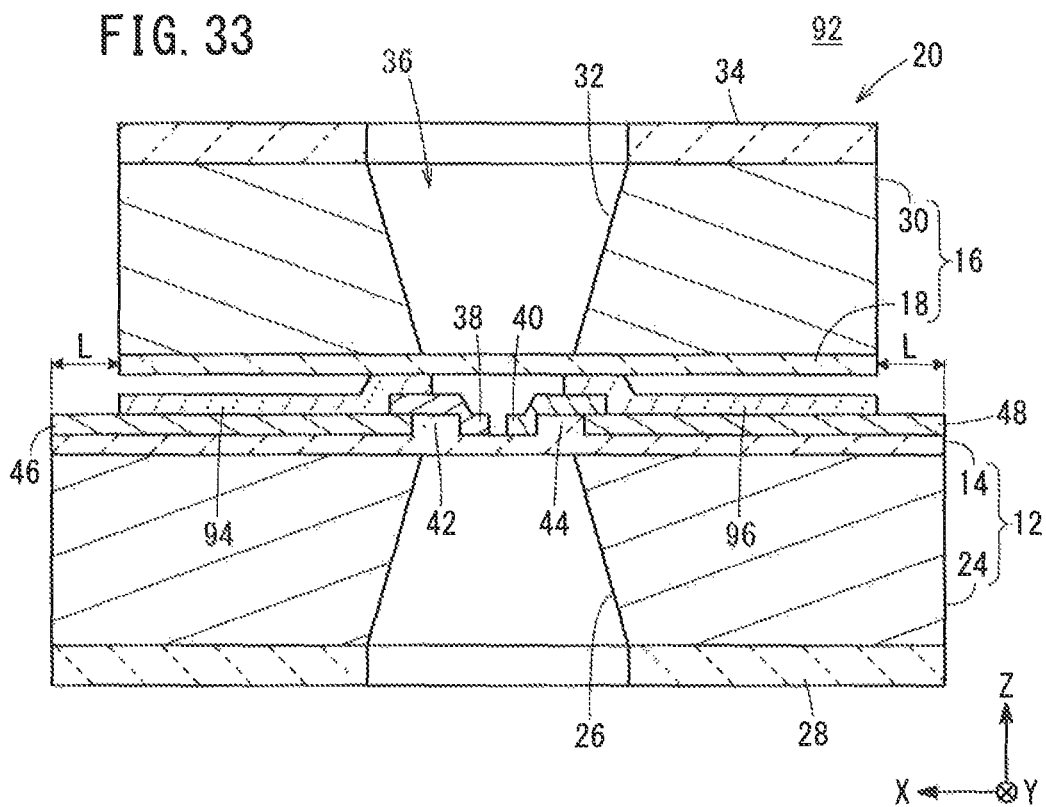

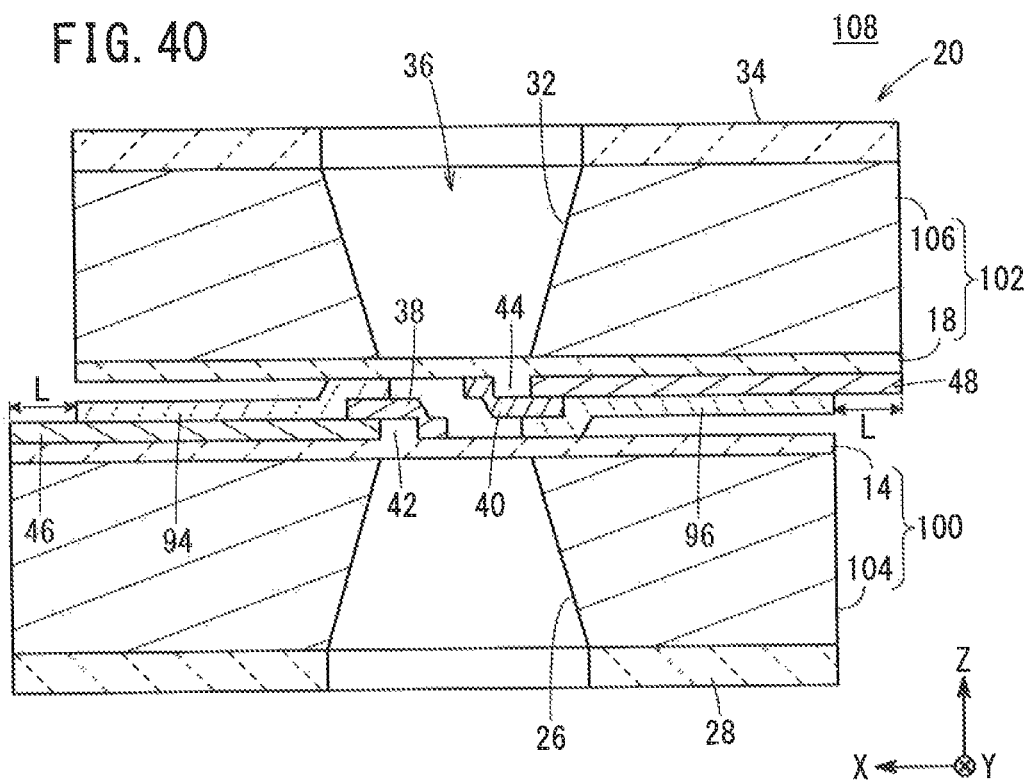

ANALYTICAL CELL

CROSS-REFERENCE TO RELATED APPLICATION

This application is based upon and claims the benefit of priority from Japanese Patent Application No. 2014-080430 filed on Apr. 9, 2014, the contents of which are incorporated herein by reference.

BACKGROUND OF THE INVENTION

1. Field of the Invention

The present invention relates to an analytical cell suitable for use, e.g., in an electrode reaction analysis in an analytical equipment.

2. Description of the Related Art

As is well known, in an electric cell, a negative electrode active material and a positive electrode active material undergo electrode reactions in the charge-discharge process. In recent years, the electrode reactions have been analyzed during the charge-discharge process using analytical equipment. For example, an analytical cell that can be observed by a transmission electron microscope (TEM) has been proposed in In-situ Electron Microscopy of Electrical Energy Storage Materials [online], 2014, Retrieved on Jan. 30, 2014 from the Internet <URL: http://www1.eere.energy.gov/vehiclesandfuels/pdfs/merit_review_2011/electrochemical_storage/es095_unocic_2011_o.pdf>.

This analytical cell contains a pair of silicon substrates, each of which has a rectangular observation window having a size of about 50 μm×100 μm. The silicon substrates are stacked at a predetermined distance from each other to form an overlapping portion in such a manner that the observation windows face each other. A negative electrode active material containing a highly oriented graphite and a positive electrode active material containing $LiCoO_2$ are located between the observation windows.

Specifically, on one of the silicon substrates, a negative electrode collector and a positive electrode collector are disposed outside of the observation window. The negative electrode collector extends from the inside of the overlapping portion and is exposed to the outside. The negative electrode active material and the positive electrode active material are formed in a plate shape by an ion beam deposition method, and extend from the negative electrode collector and the positive electrode collector to the inside of the observation window, respectively, in the overlapping portion. Incidentally, the negative electrode active material and the positive electrode active material having the plate shape are each extracted from a bulk body using a focused ion beam (FIB). Thus, the negative electrode active material and the positive electrode active material are electrically connected to the negative electrode collector and the positive electrode collector, respectively. Therefore, the negative electrode active material and the positive electrode active material can be electrically connected to an external circuit such as a charge-discharge tester by the exposed portions of the negative electrode collector and the positive electrode collector formed outside of the overlapping portion.

The electrode reactions and the like of the negative electrode active material and the positive electrode active material can be analyzed by observing the analytical cell using the transmission electron microscope (TEM). Specifically, first, the analytical cell is placed in an end of a TEM holder having a passage for introducing an electrolytic solution to the overlapping portion. Then, the electrolytic solution is introduced from the passage of the TEM holder into the overlapping portion, and the exposed portions of the negative electrode collector and the positive electrode collector formed outside of the overlapping portion are each connected to a charge-discharge tester or the like, whereby the negative electrode active material and the positive electrode active material undergo the electrode reactions. The TEM observation is carried out while transmitting an electron beam through the observation window to analyze the electrode reactions of the negative electrode active material and the positive electrode active material.

SUMMARY OF THE INVENTION

As described above, in the observation of the electrode reactions and the like on the negative electrode active material and the positive electrode active material in the analytical cell, it is necessary to transmit the electron beam through the observation windows. However, in this process, the electron beam transmission may be inhibited by the electrolytic solution. Furthermore, when the electrolytic solution is irradiated with the electron beam for a long time, the electrolytic solution may react with the electron beam, and the electron beam transmission may be inhibited also by the reaction product. In a case where the electron beam transmission is inhibited in the observation windows, the resolution of the obtained TEM observation image is deteriorated, and the observation of the electrode reactions and the like cannot be accurately performed in the analytical cell. Therefore, it is preferred that the electron beam transmission distance in the electrolytic solution in the observation windows, i.e. the thickness of the electrolytic solution layer in the observation windows, is reduced to improve the observation accuracy in the analytical cell.

However, in the above-described analytical cell, it is necessary to flow the electrolytic solution in the overlapping portion and to bring the electrolytic solution into contact with the negative electrode active material and the positive electrode active material, thereby causing the electrode reactions. When the pressure of the electrolytic solution is excessively increased, the components of the analytical cell may be broken. Therefore, to avoid this problem, the distance between the silicon substrates has to be increased to maintain a satisfactory passage for the electrolytic solution. In this case, also the thickness of the electrolytic solution layer is inevitably increased in the observation windows.

In addition, as described above, the negative electrode active material and the positive electrode active material have the plate shapes extending from the negative electrode collector and the positive electrode collector, respectively, and are interposed between the observation windows. The observation windows are located on the electrolytic solution layers formed on both ends of the negative electrode active material and the positive electrode active material in the electron beam transmission direction. Thus, the electrolytic solution layer has to be formed on each end of the negative electrode active material and the positive electrode active material in the electron beam transmission direction. Therefore, the total thickness of the electrolytic solution layers is increased in the observation windows.

Consequently, in the above-described analytical cell, the total thickness of the electrolytic solution layers cannot be satisfactorily reduced in the observation windows, and the observation accuracy can hardly be satisfactorily improved in the electrode reaction observation.

A principal object of the present invention is to provide an analytical cell capable of reducing an electron beam transmission distance through the electrolytic solution in an observation window, thereby highly accurately analyzing electrode reactions of a negative electrode active material and a positive electrode active material.

According to an aspect of the present invention, there is provided an analytical cell, through which an electron beam is transmitted to perform an analysis, comprising a first holder and a second holder stacked with an electrolytic solution interposed therebetween, wherein the first holder and the second holder each contain a substrate including a through-hole and a transmission membrane having an electron beam permeability, the through-hole extends in a thickness direction of the substrate, the transmission membrane is disposed on one surface of the substrate, such that one end of the through-hole is covered with the transmission membrane, the first holder and the second holder are stacked to form an overlapping portion in such a manner that the surfaces of the substrates with the transmission membranes formed thereon face each other, in the overlapping portion, an inner space containing the electrolytic solution is sealed, and the through-holes face each other across the transmission membranes to form an observation window, through which an electron beam is transmitted, a negative electrode active material and a positive electrode active material are arranged at a distance from each other and respectively in contact with the electrolytic solution between the transmission membranes in the observation window, and a transmission body containing an electron beam permeable solid is formed between at least one of the negative electrode active material and the positive electrode active material and the transmission membrane in the observation window.

In the analytical cell of the present invention, since the electron beam permeable transmission body is formed between at least one of the negative electrode active material and the positive electrode active material and the transmission membrane in the observation window, the transmission distance of the electron beam in the electrolytic solution can be shortened in the observation window. In other words, the thickness of the electrolytic solution layer can be reduced in the observation window, while the electron beam transmission may be inhibited by the electrolytic solution layer.

Furthermore, since the inner space containing the electrolytic solution is sealed in the overlapping portion, the negative electrode active material and the positive electrode active material can be in contact with the electrolytic solution without additionally introducing the electrolytic solution into the overlapping portion. Thus, it is not necessary to form a passage of the electrolytic solution in the overlapping portion. Therefore, the distance between the first holder and the second holder can be shortened, and the electrolytic solution layer can be thinned in the observation window.

In addition, as described above, since the electrolytic solution layer can be thinned, only a small amount of the electrolytic solution reacts with the electron beam. Therefore, generation of a reaction product derived from the electrolytic solution and the electron beam can be suppressed.

Consequently, in the analytical cell, inhibition of the electron beam transmission by the electrolytic solution or the reaction product can be suppressed, and the electron beam can be satisfactorily transmitted in the observation window. Thus, for example, a TEM observation image can be obtained with an improved resolution, and the electrode reactions and the like can be observed highly accurately.

In the above analytical cell, the negative electrode active material, the positive electrode active material, and the transmission body may be formed on the first holder. In this case, in production of the analytical cell, the negative electrode collector, the positive electrode collector, and the transmission body may be formed only on the first holder. Therefore, the analytical cell can be easily and efficiently obtained by a simple production process.

In the above analytical cell, the negative electrode active material may be formed on the first holder, the positive electrode active material may be formed on the second holder, and the transmission body may be formed on at least one of the first holder and the second holder. In this case, the negative electrode active material and the positive electrode active material are formed on the first holder and the second holder, respectively. Therefore, even when the negative electrode active material and the positive electrode active material are disposed in a small space, the negative electrode active material and the positive electrode active material are not arranged excessively close to each other and are not in contact with each other. Consequently, the negative electrode active material and the positive electrode active material can be effectively prevented from short-circuiting.

In the above analytical cell, it is preferred that the analytical cell further comprises a negative electrode collector and a positive electrode collector, the negative electrode collector and the positive electrode collector are electrically connected to the negative electrode active material and the positive electrode active material respectively in the overlapping portion, the negative electrode collector and the positive electrode collector each extend from inside of the overlapping portion and are exposed to outside, and at least one of the negative electrode collector and the positive electrode collector has an isolation membrane configured to avoid contact with the electrolytic solution in the overlapping portion.

In this case, the contact of the positive electrode collector and the negative electrode collector with the electrolytic solution is avoided in the overlapping portion. Therefore, side reactions, which are different from the electrode reactions of the negative electrode active material and the positive electrode active material, can be suppressed on the negative electrode collector and the positive electrode collector. Consequently, the analysis of the subject electrode reactions is not inhibited by the side reaction, and the observation can be more highly accurately performed in the analytical cell.

The above and other objects, features and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 1 is an overall schematic perspective view of an analytical cell according to a first embodiment of the present invention;

FIG. 2 is a cross-sectional view of the analytical cell of FIG. 1 taken along the line II-II in the direction of the arrows;

FIG. 3 is a plan view of a transmission membrane side of a first holder in the analytical cell of FIG. 1;

FIG. 4 is a plan view of a transmission membrane side of a second holder in the analytical cell of FIG. 1;

FIG. 5 is a cross-sectional view of an analytical cell according to a modification example of FIG. 1 taken in the same direction as FIG. 2;

FIG. 8A is a plan view of collector-shaped portions formed by patterning the photoresist of FIG. 7A, so that the transmission membrane precursor is exposed in the portions, FIG. 8B is a cross-sectional view taken along the line VIIIB-VIIIB in FIG. 8A in the direction of the arrows, and FIG. 8C is a cross-sectional view taken along the line VIIIC-VIIIC in FIG. 8A in the direction of the arrows;

FIG. 13A is a plan view of photoresist residues remaining only on the negative electrode collector, the positive electrode collector, and portions corresponding to transmission bodies and spacers formed by patterning the photoresist of FIG. 12A, FIG. 13B is a cross-sectional view taken along the line XIIIB-XIIIB in FIG. 13A in the direction of the arrows, and FIG. 13C is a cross-sectional view taken along the line XIIIC-XIIIC in FIG. 13A in the direction of the arrows;

FIG. 16A is a plan view of a photoresist formed on the one surface of the substrate of FIG. 15A, FIG. 16B is a cross-sectional view taken along the line XVIB-XVIB in FIG. 16A in the direction of the arrows, and FIG. 16C is a cross-sectional view taken along the line XVIC-XVIC in FIG. 16A in the direction of the arrows;

FIG. 30A is a plan view of a resultant obtained by removing the exposed portion of the covering membrane precursor, exposed in the photoresist of FIG. 29A, FIG. 30B is a cross-sectional view taken along the line XXXB-XXXB in FIG. 30A in the direction of the arrows, and FIG. 30C is a cross-sectional view taken along the line XXXC-XXXC in FIG. 30A in the direction of the arrows;

FIG. 33 is a cross-sectional view of an analytical cell according to a second embodiment of the present invention taken in the same direction as FIG. 2;

FIG. 40 is a cross-sectional view of an analytical cell according to a fourth embodiment of the present invention taken in the same direction as FIGS. 2 and 36.

DESCRIPTION OF THE PREFERRED EMBODIMENTS

Figure 6A:
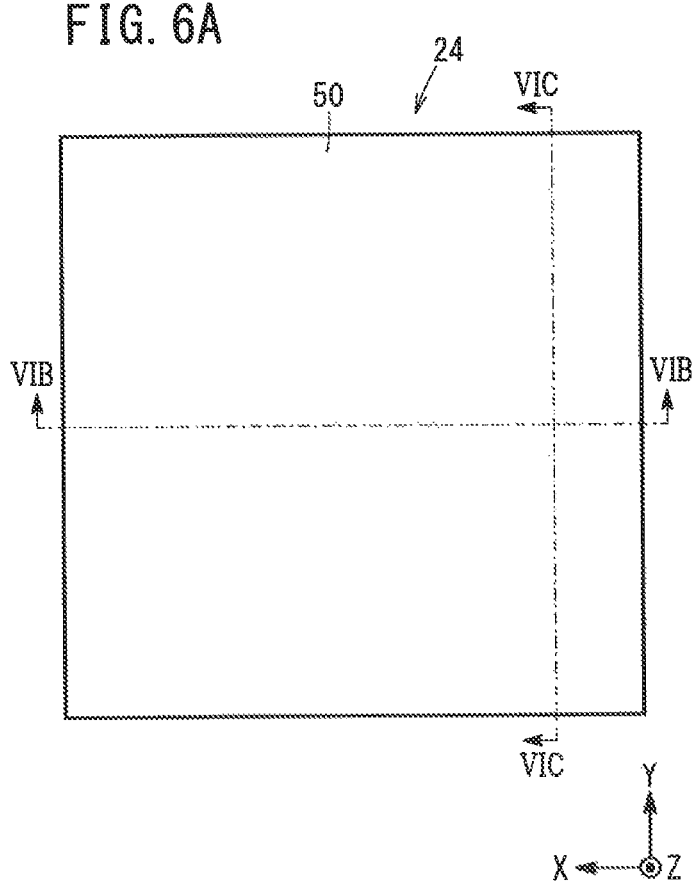
FIG. 6A is a plan view of a transmission membrane precursor side of a substrate with a transmission membrane precursor formed on one surface and a covering membrane precursor formed on the other surface.

Several preferred embodiments of the analytical cell of the present invention will be described in detail below with reference to the accompanying drawings.

The analytical cell is suitable for use, e.g., in an analysis of electrode reactions in a negative electrode active material and a positive electrode active material under electron beam transmission in analytical equipment. For example, the analytical equipment may be a transmission electron microscope (TEM). In this case, the analytical cell is attached to an end of a TEM holder, and then an observation process is performed. For example, the observation subject (i.e., the analytical cell) may be a lithium-ion secondary cell, a nickel-hydrogen cell, an alkaline-manganese cell, or the like. Examples of the analytical cell of the lithium-ion secondary cell will be described below.

First Embodiment

An analytical cell 10 according to a first embodiment will be described below with reference to FIGS. 1 to 4. FIG. 1 is an overall schematic perspective view of the analytical cell 10. FIG. 2 is a cross-sectional view taken along the line II-II in FIG. 1 in the direction of the arrows. FIG. 3 is a plan view of a transmission membrane (electron beam permeable membrane or electron beam transparent membrane) 14 side of a first holder 12 in the analytical cell 10. FIG. 4 is a plan view of a transmission membrane (electron beam permeable membrane or electron beam transparent membrane) 18 side of a second holder 16 in the analytical cell 10. To facilitate understanding, the X-axis, Y-axis, and Z-axis directions shown in FIGS. 1 to 4 are defined as the width, depth, and height directions respectively in the following description. In addition, in the X-axis, Y-axis, and Z-axis directions, the tip of the arrow is defined as one end, and the base end of the arrow is defined as the other end.

The analytical cell 10 contains the first holder 12 and the second holder 16 stacked with an electrolytic solution interposed therebetween. Specifically, the first holder 12 and the second holder 16 are stacked to form an overlapping portion 20, and spacers 11 (see FIGS. 2 and 3) for forming a space are interposed therebetween. The overlapping portion 20 is sealed by a sealant 22 such as an epoxy-based resin adhesive (see FIG. 1) while the space is filled with the electrolytic solution. Incidentally, the sealant 22 is omitted in FIG. 2. For example, the electrolytic solution enclosed (stored) in the overlapping portion 20 preferably contains propylene carbonate (PC), ethylene carbonate (EC), dimethyl carbonate (DMC), diethyl carbonate (DEC), or the like.

As shown in FIGS. 2 and 3, the first holder 12 contains a substrate 24 (see FIG. 2) and the transmission membrane 14. For example, the substrate 24 contains silicon (Si), borosilicate glass, quartz ($SiO_2$), or the like. A through-hole 26 penetrating in the thickness direction is formed approximately at the center of the substrate 24. The transmission membrane 14 is formed on one surface of the substrate 24 to cover the through-hole 26, and a covering membrane 28 (see FIG. 2) is formed on the other surface of the substrate 24, such that the through-hole 26 is exposed. The through-hole 26 has a truncated quadrangular pyramid shape tapered in the direction from the covering membrane 28 toward the transmission membrane 14 of the substrate 24.

For example, the transmission membrane 14 contains a material having an electron beam permeability (electron beam transparency) such as silicon nitride ($Si_3N_4$), silicon carbide (SiC), silicon (Si), carbon (C), or graphite (C). The covering membrane 28 may contain the same material as the transmission membrane 14.

As shown in FIGS. 2 and 4, the second holder 16 contains a substrate 30 (see FIG. 2) and the transmission membrane 18. The substrate 30 contains the same material as the substrate 24, has approximately the same depth and height as the substrate 24, and has a width smaller by 2 L (L×2) than that of the substrate 24. A through-hole 32 penetrating in the thickness direction is formed approximately at the center of the substrate 30, and has the same shape as the through-hole 26. The transmission membrane 18 is formed on one surface of the substrate 30 to cover the through-hole 32, and a covering membrane 34 (see FIG. 2) is formed on the other surface of the substrate 30, such that the through-hole 32 is exposed. The transmission membrane 18 and the covering membrane 34 may contain the same material as the transmission membrane 14.

The first holder 12 and the second holder 16 are stacked to form the overlapping portion 20 in such a manner that the through-holes 26, 32 face each other across the transmission membranes 14, 18. Since the substrate 24 has a width larger by 2 L than that of the substrate 30 as described above, the width direction end portions having a width of L in the first holder 12 are exposed and extended from the overlapping portion 20 formed in this manner (see FIGS. 1 and 2).

In the overlapping portion 20, an observation window 36, through which an electron beam is satisfactorily transmitted in the height direction, is formed in the overlap of the through-hole 26 and the transmission membrane 14 in the first holder 12 and the through-hole 32 and the transmission membrane 18 in the second holder 16. In the analytical cell 10, a negative electrode active material 38 and a positive electrode active material 40 are arranged at a distance from each other while being in contact with the electrolytic solution between the transmission membranes 14, 18 in the observation window 36, so that the electrode reactions and the like are analyzed using the electron beam transmission through the observation window 36. The overlapping portion 20 other than the observation window 36, i.e. the portion in which the substrates 24, 30 face each other across the transmission membranes 14, 18, is referred to also as the facing portion in the following description.

Specifically, as shown in FIGS. 2 and 3, both of the negative electrode active material 38 and the positive electrode active material 40 are formed on the transmission membrane 14 in the first holder 12. Transmission bodies 42, 44, a negative electrode collector 46, a positive electrode collector 48, and the spacers 11 are further formed on the transmission membrane 14.

For example, the spacers 11 contain an electrically insulating material, have a cuboid shape, and are positioned around four corners of the overlapping portion 20. The arrangement and the shape of the spacers 11 are not particularly limited as long as a desired space can be easily formed in the overlapping portion 20 by the spacers 11. It is not necessary to form the spacers 11 in a case where the desired space can be formed in the overlapping portion 20 without the spacers 11 as in an analytical cell 10A shown in FIG. 5. The components in FIG. 5, equal or similar in functions and effects to those in FIGS. 1 to 4, are denoted by the same reference numerals, and detailed explanations thereof are omitted. The analytical cell 10A has the same structure as the analytical cell 10 except that the spacers 11 are not formed.

The negative electrode active material 38 has a layer structure extending from the observation window 36 to the facing portion on one end side in the width direction. The negative electrode active material 38 can be preferably formed from a substance such as $Li_4Ti_5O_{12}$, C, Si, or Ge.

The positive electrode active material 40 has a layer structure extending from the observation window 36 to the facing portion on the other end side in the width direction. The positive electrode active material 40 can be preferably formed from a substance such as $LiCoO_2$, $LiMn_2O_2$, $LiNiO_2$, $LiFePO_4$, $Li_2FePO_4F$, $LiCo_{1/2}Ni_{1/2}Mn_{1/2}O_2$, or Li ($Li_\alpha N$-$i_xMn_yCo_z)O_2$.

The transmission body 42 contains an electron beam permeable solid (electron beam transparent solid), and is formed between the transmission membrane 14 and the negative electrode active material 38 in the observation window 36. Specifically, the transmission body 42 is disposed adjacent to the other end of the negative electrode collector 46 in the width direction, is formed integrally with the transmission membrane 14, and protrudes from the transmission membrane 14 to form a cuboid shape with a thickness approximately equal to that of the negative electrode collector 46. Since the negative electrode active material 38 has the layer structure extending from the negative electrode collector 46 to the transmission membrane 14 (so as to contact the transmission membrane 14), the transmission body 42 is covered with the negative electrode active material 38. The transmission body 42 may be prepared separately from the transmission membrane 14, and may be attached to the transmission membrane 14 in the observation window 36.

The transmission body 44 is formed in the same manner as the transmission body 42 except that it is located between the transmission membrane 14 and the positive electrode active material 40 in the observation window 36. Specifically, the transmission body 44 is disposed adjacent to the one end of the positive electrode collector 48 in the width direction, and has a thickness approximately equal to that of the positive electrode collector 48.

Thus, in the observation window 36, the transmission bodies 42, 44 are each located on the transmission membrane 14 in one of spaces formed at both sides of the negative electrode active material 38 and the positive electrode active material 40 in the height direction (the electron beam transmission direction). Consequently, in the analytical cell 10, the electrolytic solution layer is formed only on the side of the transmission membrane 18 of the negative electrode active material 38 and the positive electrode active material 40.

The other end of the negative electrode collector 46 in the width direction is electrically connected to the negative electrode active material 38 in the facing portion in the overlapping portion 20, and the one end in the width direction is exposed to the outside of the overlapping portion 20. In the example of FIGS. 1 to 4, the exposed portion of the first holder 12 protruding or extending from the overlapping portion 20 has the width L, and thus also the exposed portion in the one end of the negative electrode collector 46 protruding or extending from the overlapping portion 20 has the width L. The negative electrode collector 46 preferably contains a substance such as tungsten (W), copper (Cu), aluminum (Al), platinum (Pt), gold (Au), or carbon (C).

The positive electrode collector 48 has the same structure as the negative electrode collector 46 except that the one end in the width direction is electrically connected to the positive electrode active material 40 in the facing portion in the overlapping portion 20. Thus, the other end of the positive electrode collector 48 in the width direction is exposed and extended from the overlapping portion 20 by the width L.

In the negative electrode collector 46 and the positive electrode collector 48, the portions protruding from the overlapping portion 20 are hereinafter referred to also as the exposed portions.

In the analytical cell 10 having the above structure, the negative electrode active material 38 and the positive electrode active material 40 can be electrically connected to the outside of the overlapping portion 20 (e.g., an external circuit) by the negative electrode collector 46 and the positive electrode collector 48. Thus, for example, in the step of forming the sealant 22, when metal wires for electrical connection (not shown) are interposed between the exposed portions and the sealant 22, the metal wires are electrically connected to the negative electrode collector 46 and the positive electrode collector 48, respectively.

For example, the metal wires are connected to an external circuit such as a charge-discharge tester. In this case, the negative electrode active material 38 and the positive electrode active material 40 can be electrically connected to the external circuit by the negative electrode collector 46 and the positive electrode collector 48. Consequently, desired electrode reactions such as charge-discharge reactions can be carried out in the cell containing the negative electrode active material 38, the positive electrode active material 40, and the electrolytic solution.

In the analytical cell 10, since a small amount of the electrolytic solution is enclosed in the overlapping portion 20, the negative electrode active material 38 and the positive electrode active material 40 can be in contact with the electrolytic solution without additionally introducing the electrolytic solution into the overlapping portion 20. Therefore, the pressure of the electrolytic solution acting on the first holder 12 and the second holder 16, i.e. the inner pressure of the analytical cell 10, can be lowered. Consequently, it is not necessary to increase the distance between the first holder 12 and the second holder 16, the thickness of the electrolytic solution layer can be reduced in the observation window 36, and the analytical cell 10 can be a small size.

For example, in the TEM observation of the analytical cell 10, the analytical cell 10 is placed on the TEM holder in a manner such that the observation window 36 faces an electron beam irradiation part of the TEM. Then, the metal wires are connected to the charge-discharge tester or the like, and a potential difference is applied between the metal wires to cause the electrode reactions as the observation subject in the negative electrode active material 38 and the positive electrode active material 40.

The electron beam is transmitted through the observation window 36 in this state, whereby the electrode reactions and the like of the negative electrode active material 38 and the positive electrode active material 40 can be observed. The electron beam permeable transmission bodies 42, 44 are formed between the transmission membrane 14 and each of the negative electrode active material 38 and the positive electrode active material 40 as described above. Therefore, though the electron beam transmission may be inhibited by the electrolytic solution layer, the thickness of the electrolytic solution layer can be reduced. Furthermore, it is not necessary to increase the distance between the first holder 12 and the second holder 16 as described above, and the electrolytic solution layer can be thinned in the observation window 36.

Since the electrolytic solution layer can be thinned as described above, only a small amount of the electrolytic solution reacts with the electron beam. Therefore, generation of a reaction product derived from the electrolytic solution and the electron beam can be suppressed. Consequently, inhibition of the electron beam transmission by the electrolytic solution or the reaction product can be effectively suppressed, and the electron beam can be satisfactorily transmitted in the observation window 36. As a result, the observation accuracy can be effectively improved in the analytical cell 10.

For example, in a specific method using the TEM for analyzing the electrode reactions, an electron diffraction pattern is obtained based on the electron beam transmitted through the observation window 36. When the negative electrode active material 38 or the positive electrode active material 40 is physically or chemically changed in the process of the electrode reaction, the change is shown in the electron diffraction pattern. Therefore, information on the changes of the negative electrode active material 38 and the positive electrode active material 40 can be obtained by observing the electron diffraction pattern during the electrode reactions. In this embodiment, the electron beam transmission through the electrolytic solution layer can be reduced, and the information accuracy deterioration due to the above-described reaction product can be prevented. Thus, so-called in-situ observation can be performed highly accurately.

The analytical cell 10 may be produced by a known semiconductor process (see, e.g., International Publication No. WO 2008/141147). A method for producing the analytical cell 10 will be described below with reference to FIGS. 6A to 32C.

The analytical cell 10 may be produced by separately preparing the first holder 12 and the second holder 16, and then by combining the first holder 12 and the second holder 16. First, a method for preparing the first holder 12 will be described below. In the following example, the substrate 24 and the negative electrode active material 38 are made of silicon (Si), the transmission membrane 14 and the covering membrane 28 are made of silicon nitride ($Si_3N_4$), the negative electrode collector 46 and the positive electrode collector 48 are made of tungsten (W), and the positive electrode active material 40 is made of lithium cobaltate ($LiCoO_2$).

Figure 6C:
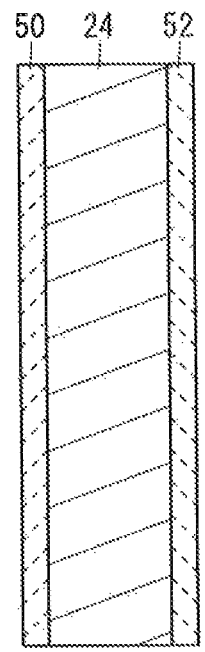
FIG. 6C is a cross-sectional view taken along the line VIC-VIC in FIG. 6A in the direction of the arrows.
Figure 6B:
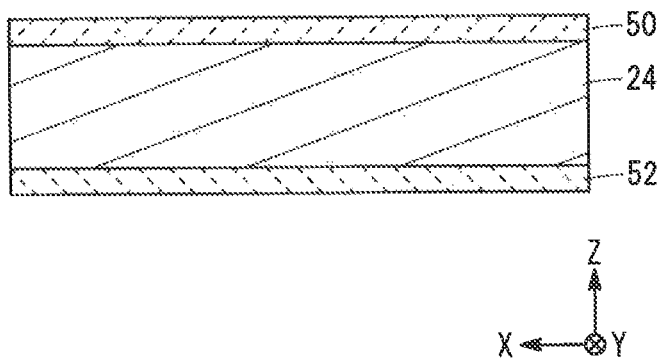
FIG. 6B is a cross-sectional view taken along the line VIB-VIB in FIG. 6A in the direction of the arrows.

First, as shown in FIGS. 6A to 6C, both surfaces of the substrate 24 are polished, and are each covered with a silicon nitride membrane by chemical vapor deposition (CVD). The silicon nitride membrane formed on the one surface of the substrate 24 is used as a precursor of the transmission membrane 14 (a transmission membrane precursor 50), and the silicon nitride membrane formed on the other surface is used as a precursor of the covering membrane 28 (a covering membrane precursor 52).

Figure 7A:
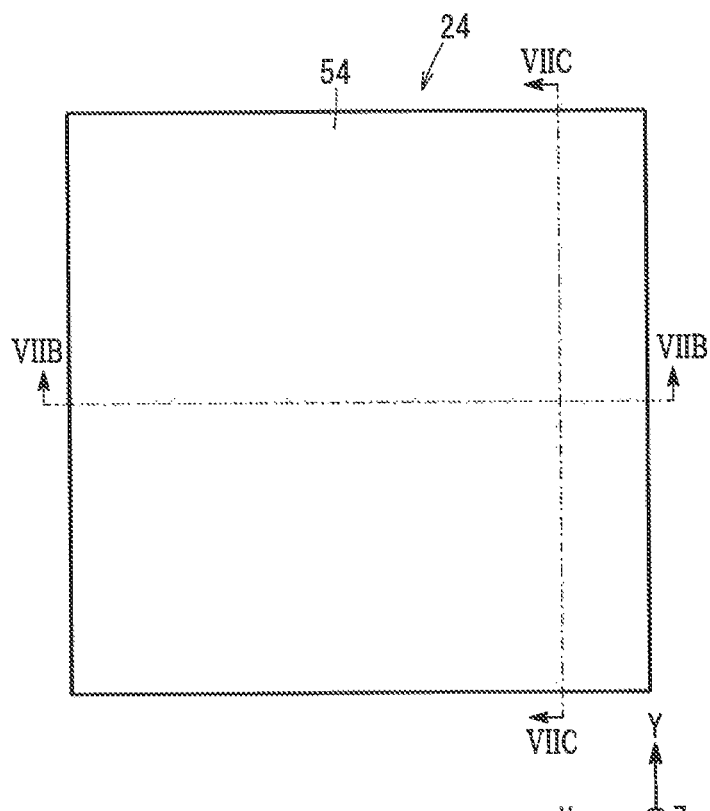
FIG. 7A is a plan view of a photoresist formed on the one surface of the substrate of FIG. 6A.
Figure 7C:
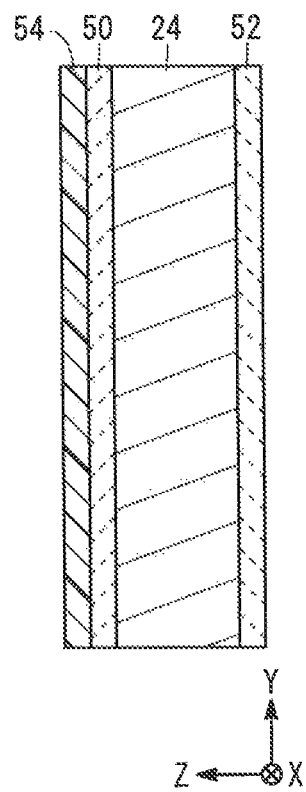
FIG. 7C is a cross-sectional view taken along the line VIIC-VIIC in FIG. 7A in the direction of the arrows.
Figure 7B:
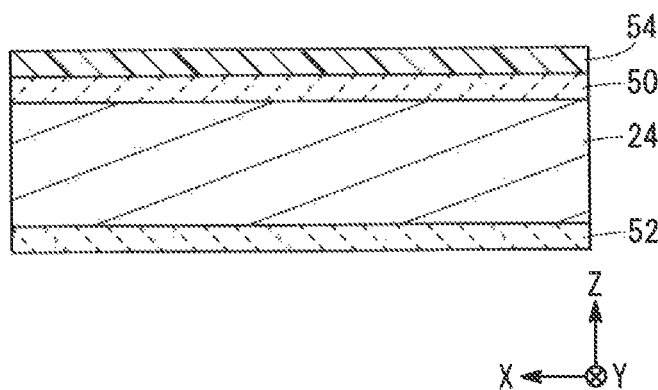
FIG. 7B is a cross-sectional view taken along the line VIIB-VIIB in FIG. 7A in the direction of the arrows.

As shown in FIGS. 7A to 7C, the transmission membrane precursor 50 is covered with a photoresist 54. As shown in FIGS. 8A to 8C, the photoresist 54 is removed by a photolithography process in portions corresponding to the negative electrode collector 46 and the positive electrode collector 48. Thus, a pair of collector-shaped portions 56, 56, which have the same shapes as the negative electrode collector 46 and the positive electrode collector 48, are formed by removing the photoresist 54, and the transmission membrane precursor 50 is exposed in the collector-shaped portions 56, 56.

Figure 9A:
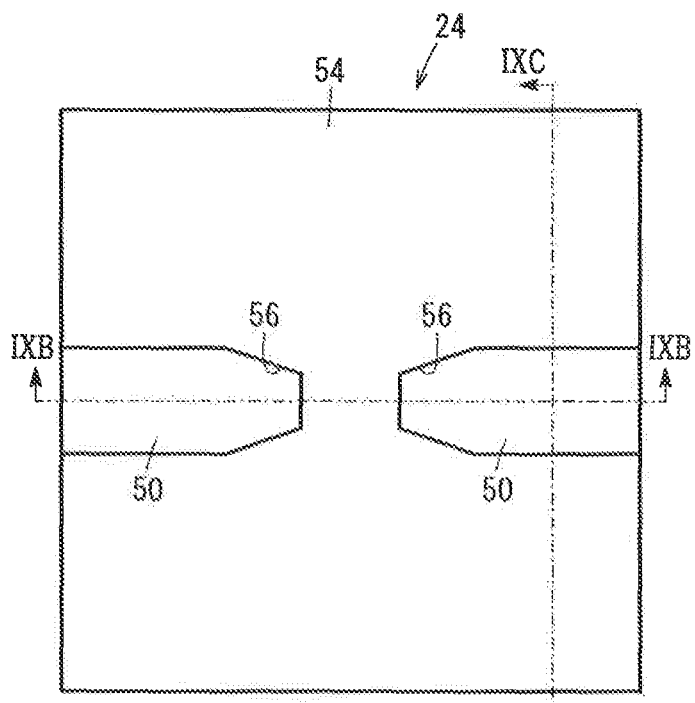
FIG. 9A is a plan view of thinned portions in the transmission membrane precursor corresponding to the collector-shaped portions of FIG. 8A.
Figure 9C:
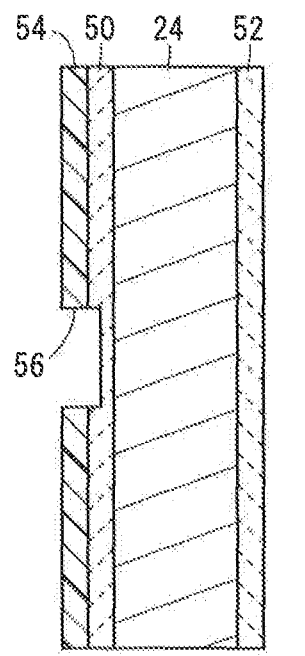
FIG. 9C is a cross-sectional view taken along the line IXC-IXC in FIG. 9A in the direction of the arrows.
Figure 9B:
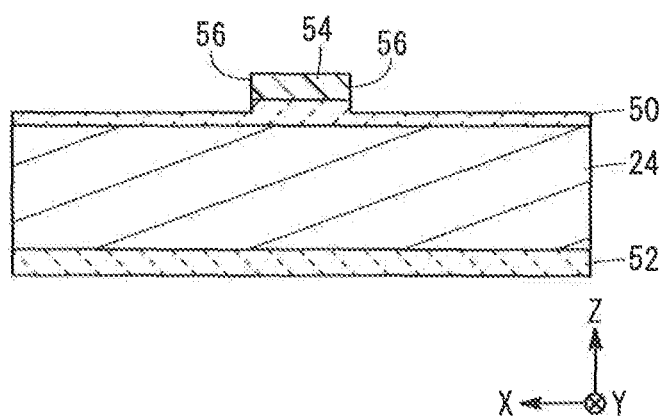
FIG. 9B is a cross-sectional view taken along the line IXB-IXB in FIG. 9A in the direction of the arrows.

As shown in FIGS. 9A to 9C, a reactive ion etching process is carried out using the photoresist 54 as a mask, whereby the height of the exposed transmission membrane precursor 50 is reduced in the collector-shaped portions 56, 56. Thus, in the transmission membrane precursor 50, the portions corresponding to the negative electrode collector 46 and the positive electrode collector 48 are thinned by the height of the negative electrode collector 46 and the positive electrode collector 48.

Figure 10A:
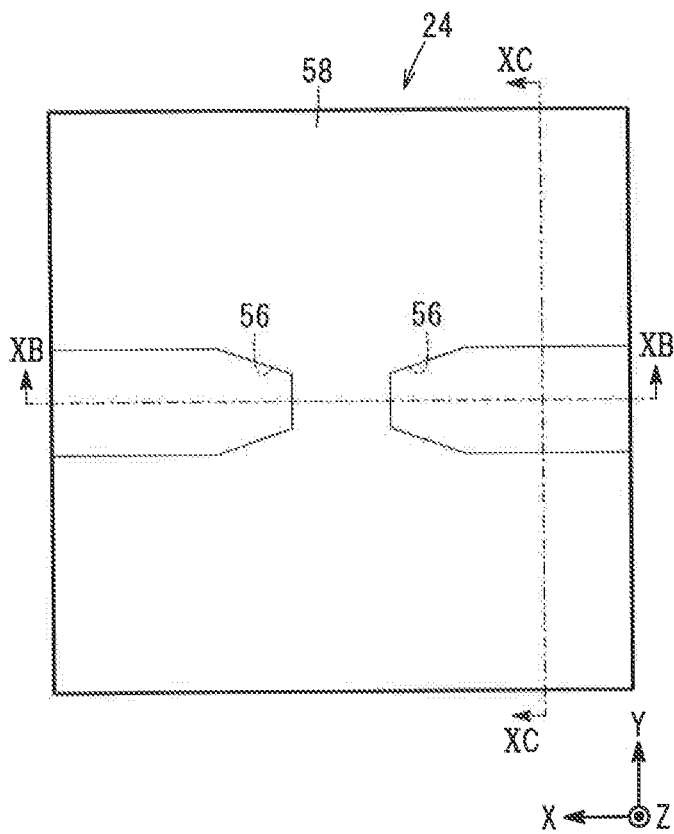
FIG. 10A is a plan view of a collector precursor formed on the one surface of the substrate of FIG. 9A.
Figure 10C:
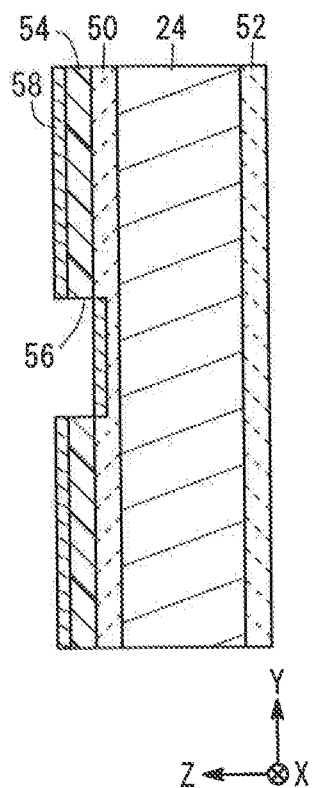
FIG. 10C is a cross-sectional view taken along the line XC-XC in FIG. 10A in the direction of the arrows.
Figure 10B:
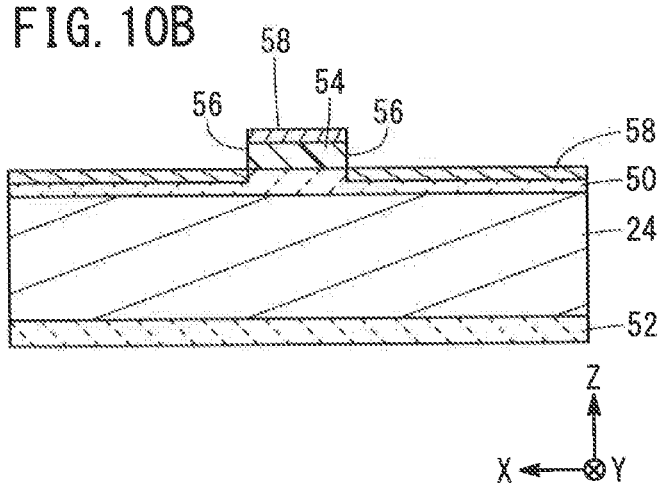
FIG. 10B is a cross-sectional view taken along the line XB-XB in FIG. 10A in the direction of the arrows.
Figure 11A:
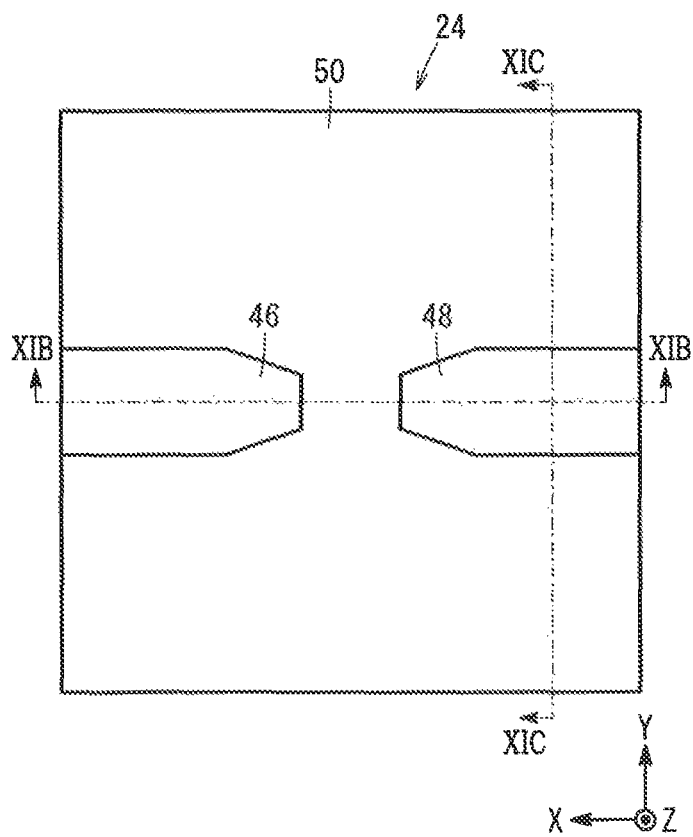
FIG. 11A is a plan view of a negative electrode collector and a positive electrode collector obtained by removing the photoresist of FIG. 10A.
Figure 11C:
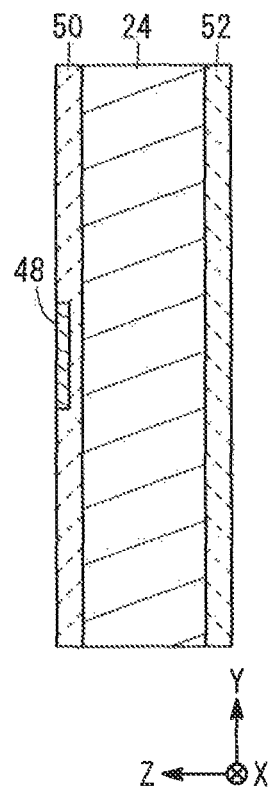
FIG. 11C is a cross-sectional view taken along the line XIC-XIC in FIG. 11A in the direction of the arrows.
Figure 11B:
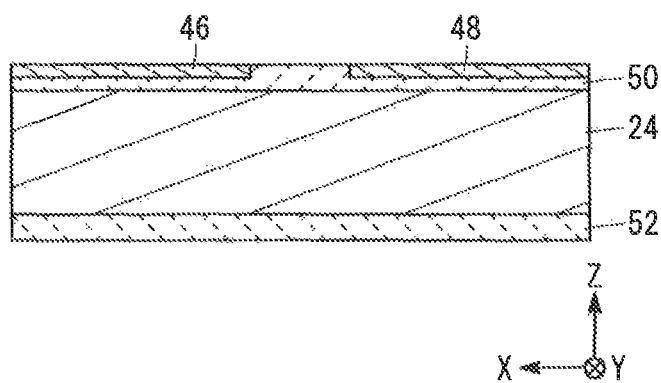
FIG. 11B is a cross-sectional view taken along the line XIB-XIB in FIG. 11A in the direction of the arrows.

As shown in FIGS. 10A to 10C, the exposed portions of the transmission membrane precursor 50 and the photoresist 54 are covered with a tungsten membrane by physical vapor deposition (PVD). The tungsten membrane is used as a precursor of the negative electrode collector 46 and the positive electrode collector 48 (a collector precursor 58). As shown in FIGS. 11A to 11C, the entire photoresist 54 is removed (lifted off), whereby the negative electrode collector 46 and the positive electrode collector 48 are formed in the thinned portions of the transmission membrane precursor 50.

Figure 12A:
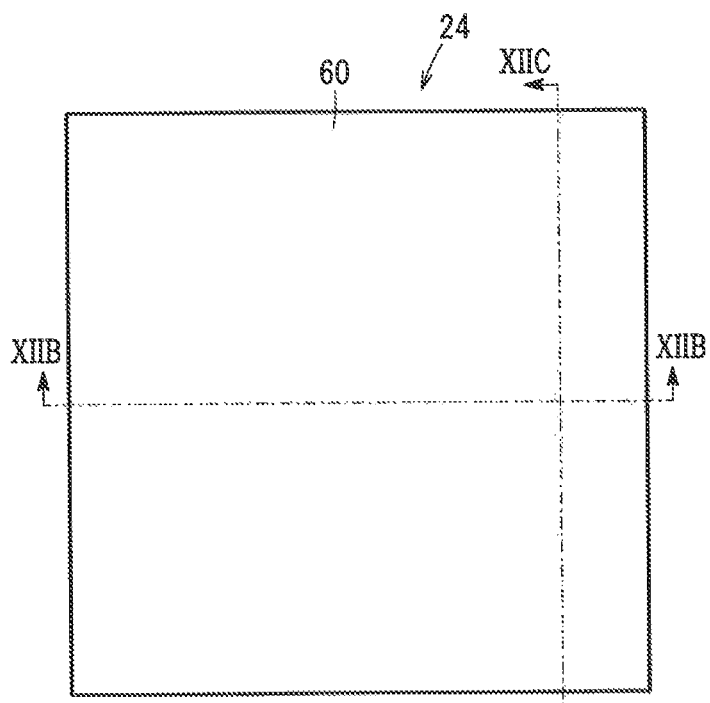
FIG. 12A is a plan view of a photoresist formed on the one surface of the substrate of FIG. 11A.
Figure 12C:
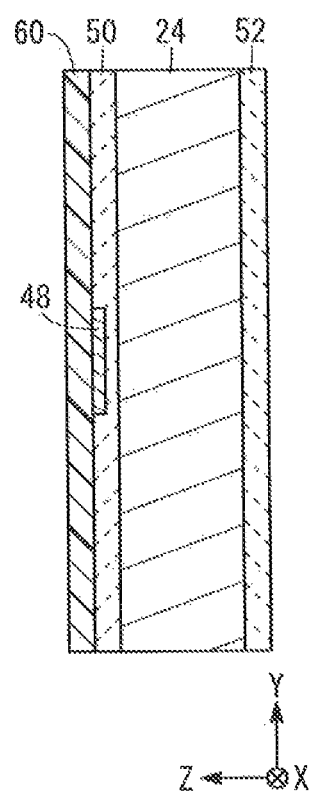
FIG. 12C is a cross-sectional view taken along the line XIIC-XIIC in FIG. 12A in the direction of the arrows.
Figure 12B:
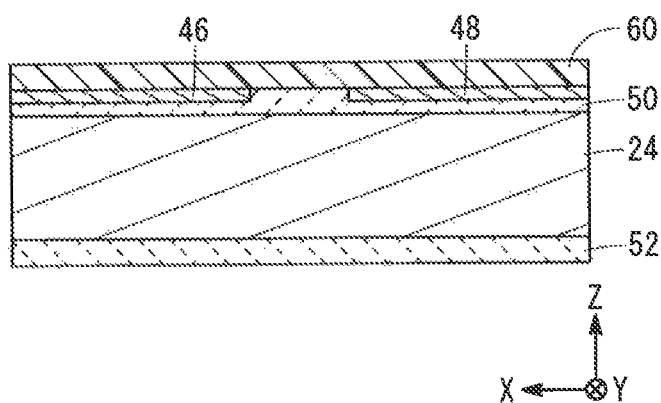
FIG. 12B is a cross-sectional view taken along the line XIIB-XIIB in FIG. 12A in the direction of the arrows.

As shown in FIGS. 12A to 12C, the one surface of the substrate 24 having the transmission membrane precursor 50, the negative electrode collector 46, and the positive electrode collector 48 is covered with a photoresist 60. As shown in FIGS. 13A to 13C, the photoresist 60 is patterned by a photolithography process, such that the photoresist 60 remains only on the negative electrode collector 46, the positive electrode collector 48, and portions corresponding to the transmission bodies 42, 44 and the spacers 11 on the transmission membrane precursor 50. Thus, transmission body formation membranes 62, 64 and spacer formation membranes 66 of the photoresist 60 are formed in the portions corresponding to the transmission bodies 42, 44 and the spacers 11.

In production of the analytical cell 10A, the spacer formation membranes 66 are not formed. Thus, the photoresist 60 is removed also in the portions corresponding to the spacers 11 in the above photolithography process.

Figure 14A:
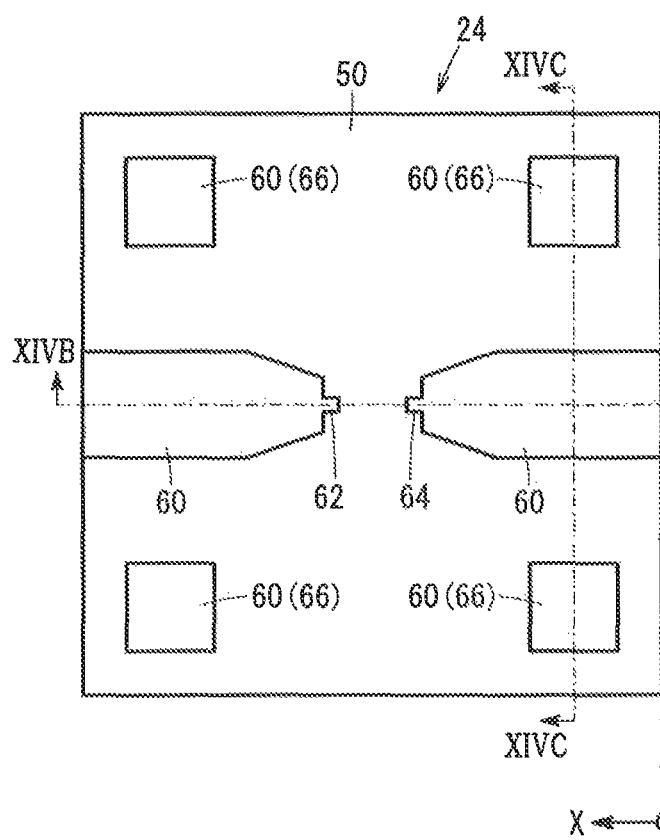
FIG. 14A is a plan view of a resultant obtained by thinning the exposed portions of the transmission membrane precursor around the photoresist residues of FIG. 13A.
Figure 14C:
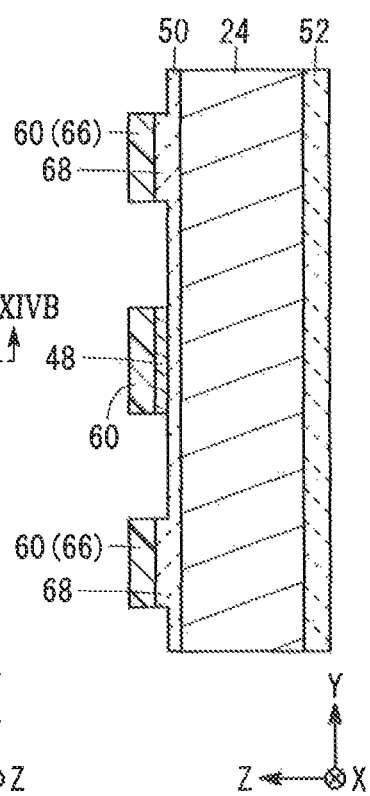
FIG. 14C is a cross-sectional view taken along the line XIVC-XIVC in FIG. 14A in the direction of the arrows.
Figure 14B:
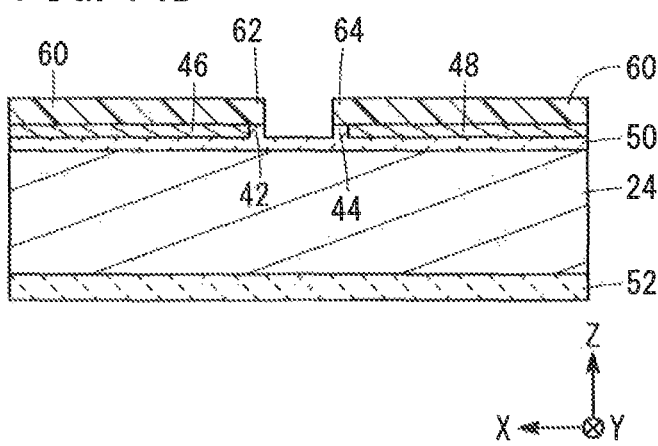
FIG. 14B is a cross-sectional view taken along the line XIVB-XIVB in FIG. 14A in the direction of the arrows.

As shown in FIGS. 14A to 14C, a reactive ion etching process is carried out using the photoresist 60 as a mask. In this process, the negative electrode collector 46 and the positive electrode collector 48 are protected by the residues of the photoresist 60, and the height of the exposed portion of the transmission membrane precursor 50 is reduced around the transmission body formation membranes 62, 64 and the spacer formation membranes 66. Thus, in the transmission membrane precursor 50, portions covered with the transmission body formation membranes 62, 64 protrude as the transmission bodies 42, 44, and portions covered with the spacer formation membranes 66 protrude as first spacer-shaped portions 68. The transmission bodies 42, 44 and the first spacer-shaped portions 68 have approximately the same height as the negative electrode collector 46 and the positive electrode collector 48.

Figure 15A:
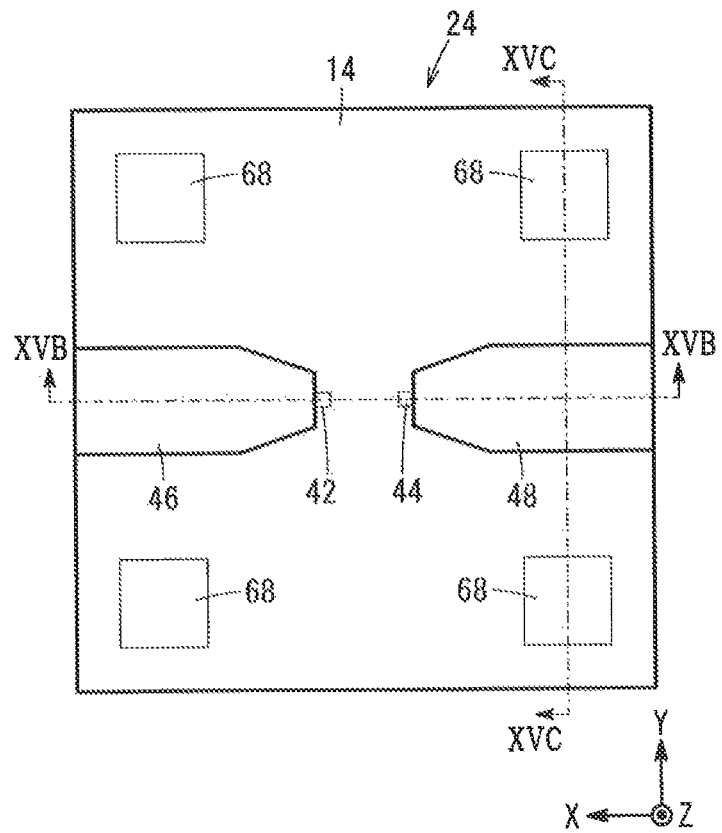
FIG. 15A is a plan view of a transmission membrane and first spacer-shaped portions of the transmission membrane precursor obtained by removing the patterned photoresist of FIG. 14A.
Figure 15C:
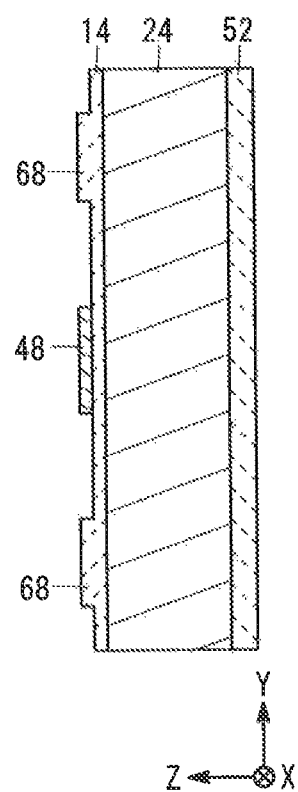
FIG. 15C is a cross-sectional view taken along the line XVC-XVC in FIG. 15A in the direction of the arrows.
Figure 15B:
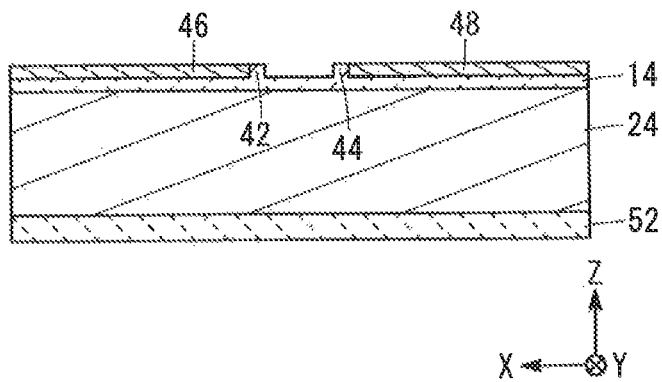
FIG. 15B is a cross-sectional view taken along the line XVB-XVB in FIG. 15A in the direction of the arrows.

As shown in FIGS. 15A to 15C, the photoresist 60 is lifted off to obtain the transmission membrane 14. Then, as shown in FIGS. 16A to 16C, the one surface of the substrate 24 having the transmission membrane 14, the transmission bodies 42, 44, the first spacer-shaped portions 68, the negative electrode collector 46 and the positive electrode collector 48 is covered with a photoresist 70.

Figure 17A:
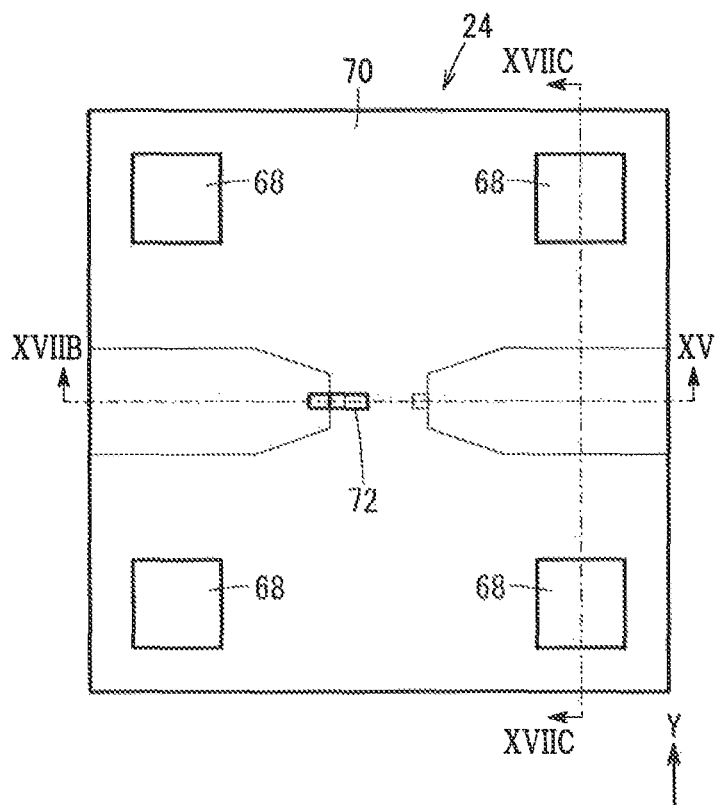
FIG. 17A is a plan view of a negative electrode active material formation portion (formed on the transmission membrane and the negative electrode collector), the transmission body, and the first spacer-shaped portions exposed by patterning the photoresist of FIG. 16A.
Figure 17C:
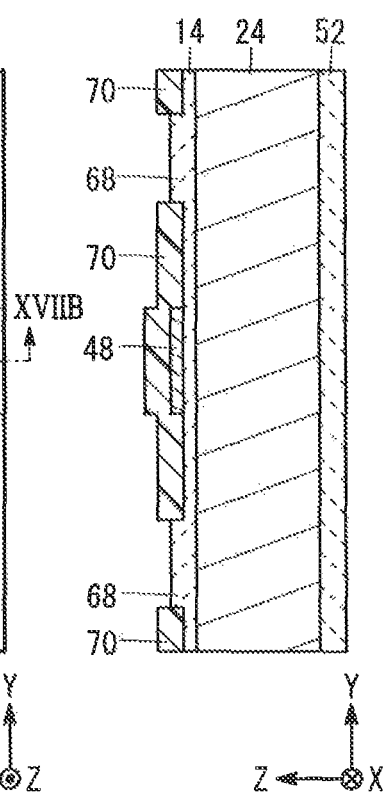
FIG. 17C is a cross-sectional view taken along the line XVIIC-XVIIC in FIG. 17A in the direction of the arrows.
Figure 17B:
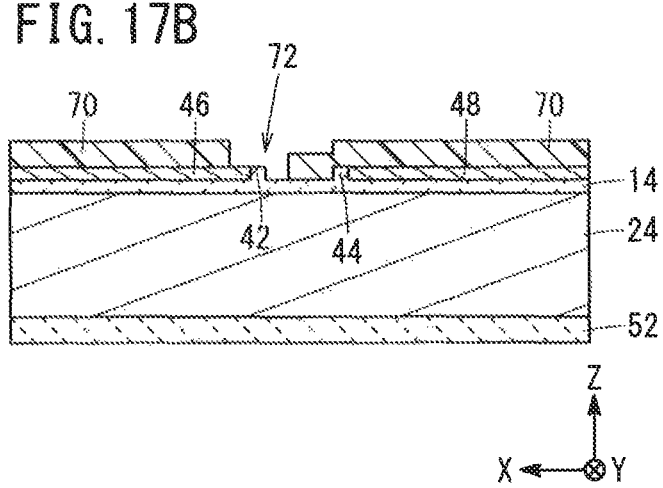
FIG. 17B is a cross-sectional view taken along the line XVIIB-XVIIB in FIG. 17A in the direction of the arrows.

As shown in FIGS. 17A to 17C, the photoresist 70 is patterned by a photolithography process, such that the first spacer-shaped portions 68 are exposed, and the transmission body 42 and a portion corresponding to the negative electrode active material 38 on the transmission membrane 14 and the negative electrode collector 46 are further exposed. Thus, a negative electrode active material formation portion 72 is formed by removing the photoresist 70 along the shape of the negative electrode active material 38.

Figure 18A:
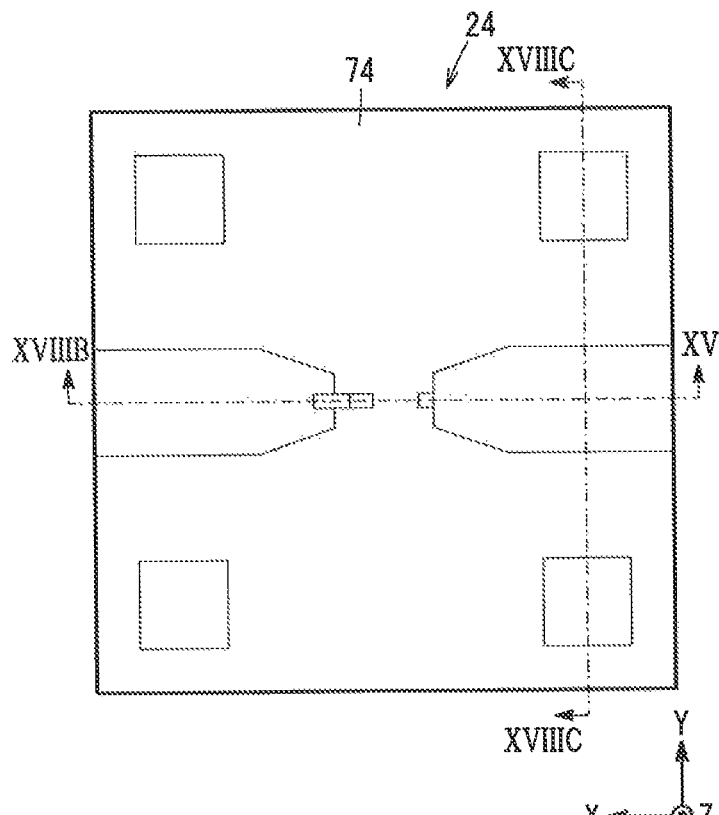
FIG. 18A is a plan view of a negative electrode active material precursor formed on the one surface of the substrate of FIG. 17A.
Figure 18C:
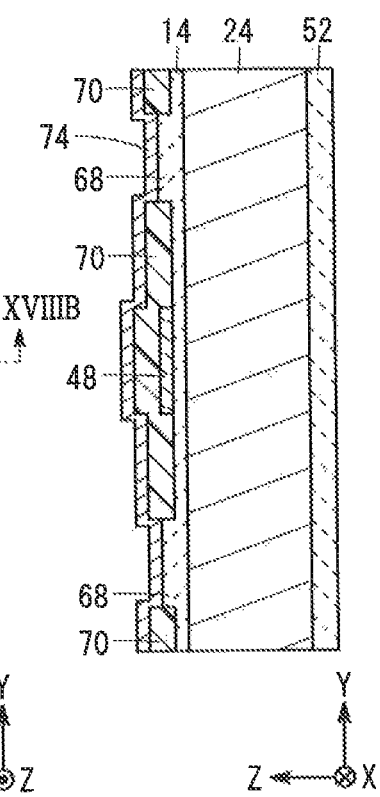
FIG. 18C is a cross-sectional view taken along the line XVIIIC-XVIIIC in FIG. 18A in the direction of the arrows.
Figure 18B:
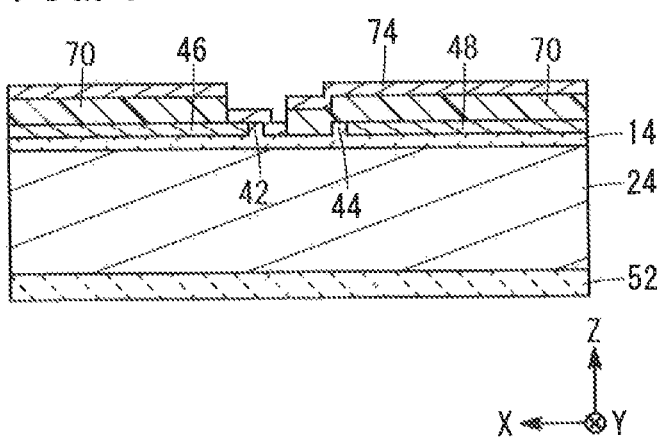
FIG. 18B is a cross-sectional view taken along the line XVIIIB-XVIIIB in FIG. 18A in the direction of the arrows.
Figure 19A:
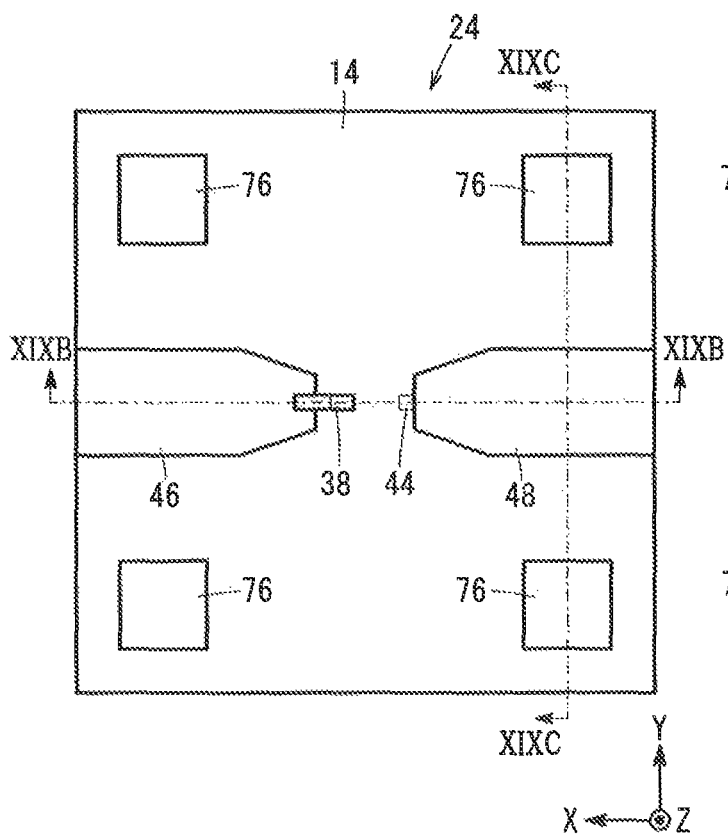
FIG. 19A is a plan view of a negative electrode active material and second spacer-shaped portions obtained by removing the photoresist of FIG. 18A.
Figure 19C:
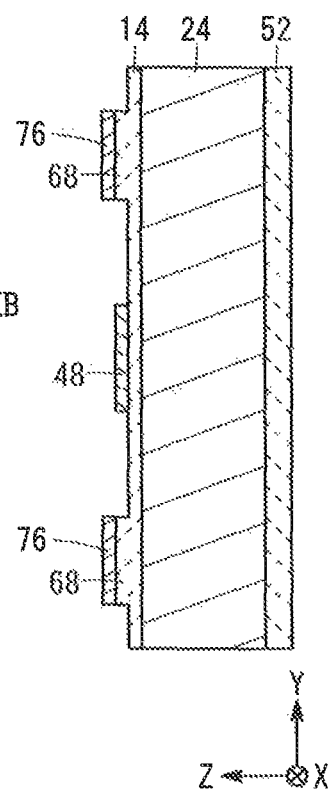
FIG. 19C is a cross-sectional view taken along the line XIXC-XIXC in FIG. 19A in the direction of the arrows.
Figure 19B:
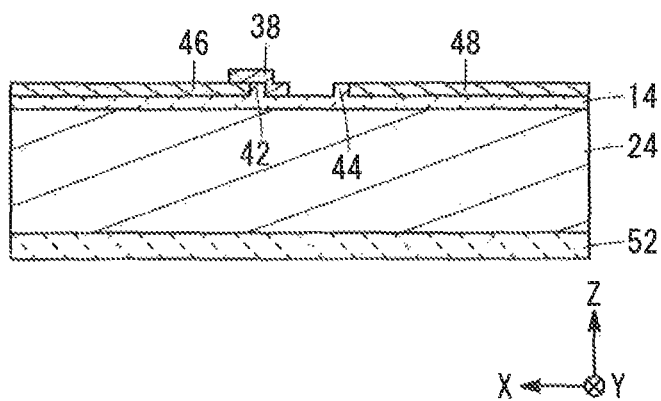
FIG. 19B is a cross-sectional view taken along the line XIXB-XIXB in FIG. 19A in the direction of the arrows.

As shown in FIGS. 18A to 18C, the one surface of the substrate 24 having the photoresist 70, the first spacer-shaped portions 68, and the negative electrode active material formation portion 72 is covered with a silicon membrane by physical vapor deposition (PVD). The silicon membrane is used as a precursor of the negative electrode active material 38 (a negative electrode active material precursor 74). As shown in FIGS. 19A to 19C, the photoresist 70 is lifted off to obtain the negative electrode active material 38. Furthermore, second spacer-shaped portions 76 are obtained from the negative electrode active material precursor 74 remaining on the first spacer-shaped portions 68.

Figure 20A:
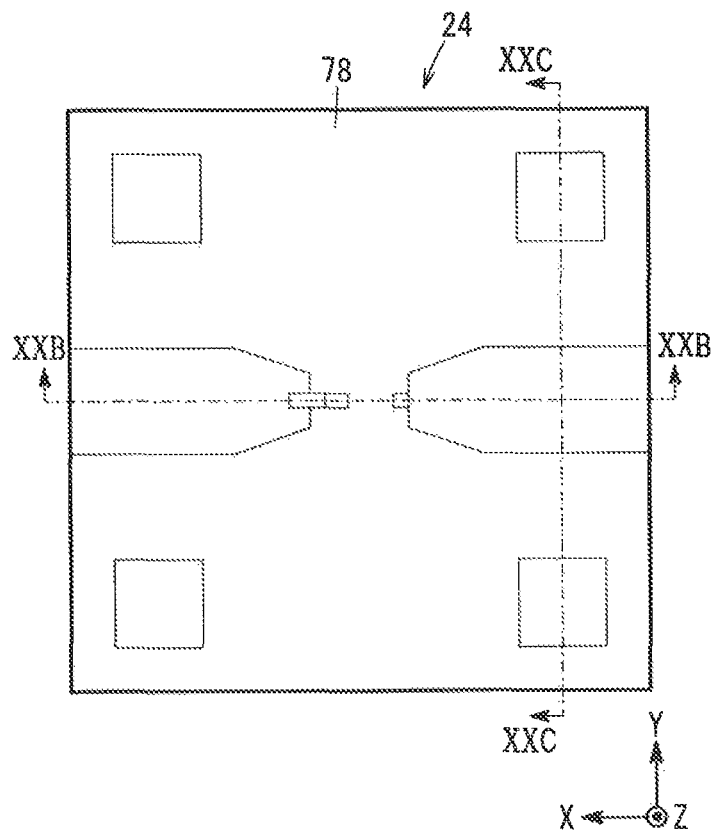
FIG. 20A is a plan view of a photoresist formed on the one surface of the substrate of FIG. 19A.
Figure 20C:
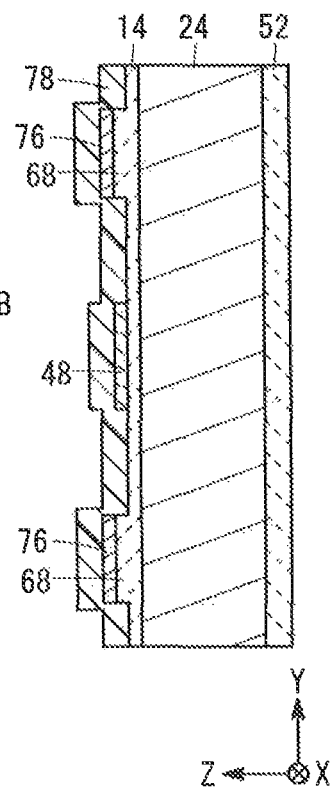
FIG. 20C is a cross-sectional view taken along the line XXC-XXC in FIG. 20A in the direction of the arrows.
Figure 20B:
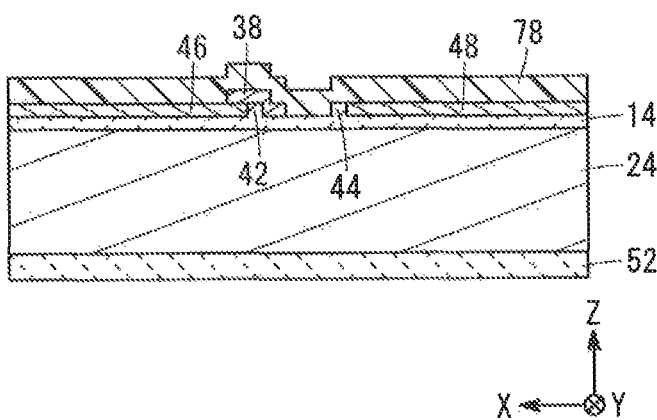
FIG. 20B is a cross-sectional view taken along the line XXB-XXB in FIG. 20A in the direction of the arrows.
Figure 21A:
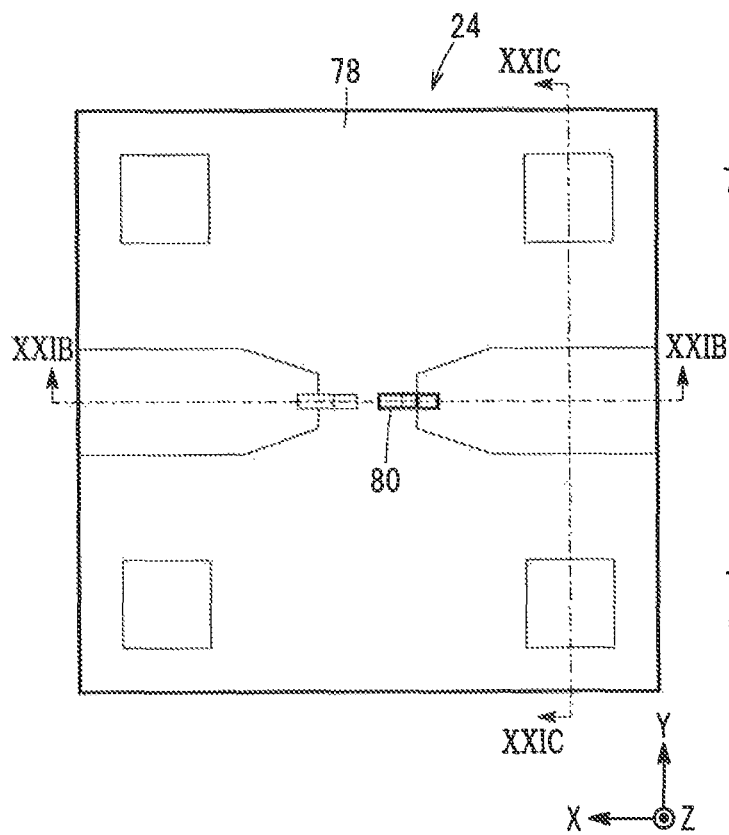
FIG. 21A is a plan view of a positive electrode active material formation portion (formed on the transmission membrane and the positive electrode collector) and the transmission body exposed by patterning the photoresist of FIG. 20A.
Figure 21C:
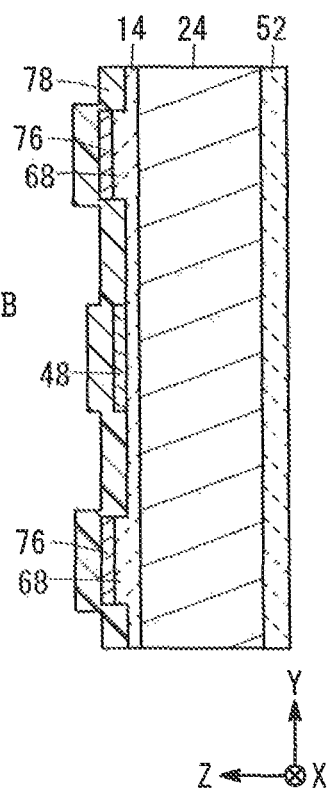
FIG. 21C is a cross-sectional view taken along the line XXIC-XXIC in FIG. 21A in the direction of the arrows.
Figure 21B:
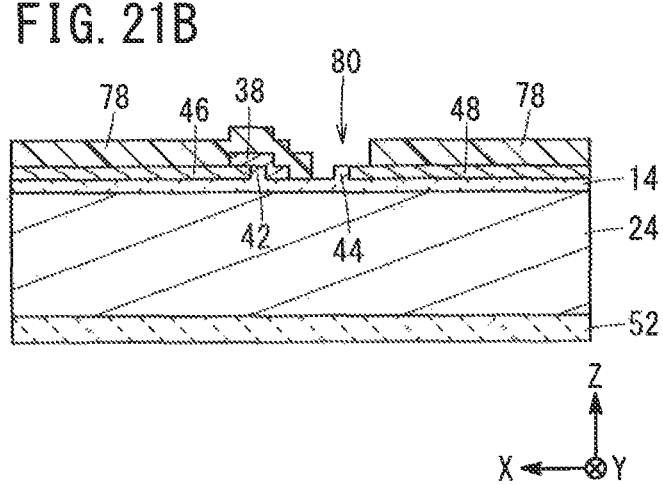
FIG. 21B is a cross-sectional view taken along the line XXIB-XXIB in FIG. 21A in the direction of the arrows.

As shown in FIGS. 20A to 20C, the one surface of the substrate 24 having the negative electrode active material 38, the negative electrode collector 46, the transmission body 44, the positive electrode collector 48, the transmission membrane 14, and the second spacer-shaped portions 76 is covered with a photoresist 78. As shown in FIGS. 21A to 21C, the photoresist 78 is patterned by a photolithography process, such that the transmission body 44 is exposed, and a portion corresponding to the positive electrode active material 40 on the transmission membrane 14 and the positive electrode collector 48 is further exposed. Thus, a positive electrode active material formation portion 80 is formed by removing the photoresist 78 along the shape of the positive electrode active material 40.

Figure 22A:
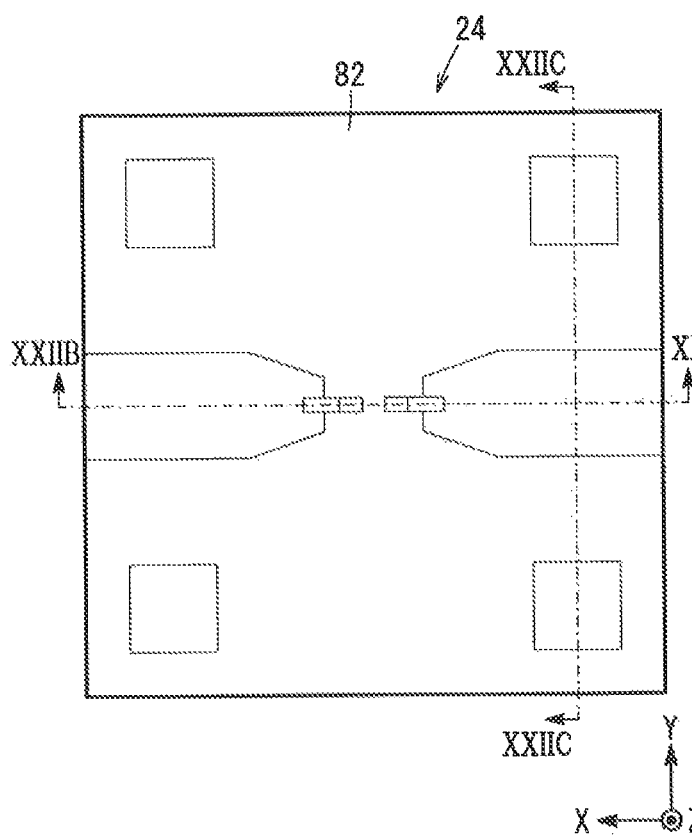
FIG. 22A is a plan view of a positive electrode active material precursor formed on the one surface of the substrate of FIG. 21A.
Figure 22C:
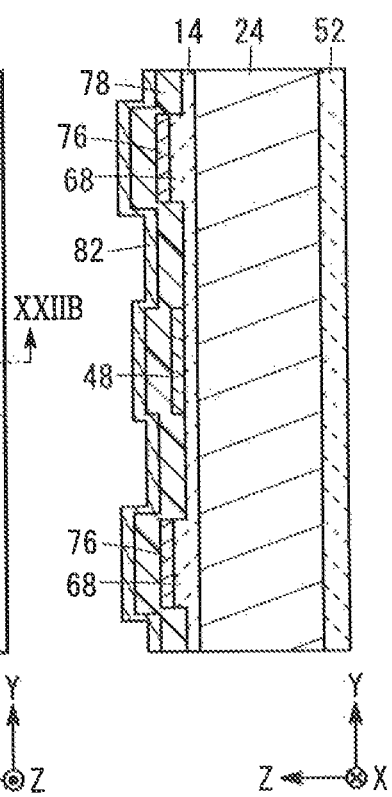
FIG. 22C is a cross-sectional view taken along the line XXIIC-XXIIC in FIG. 22A in the direction of the arrows.
Figure 22B:
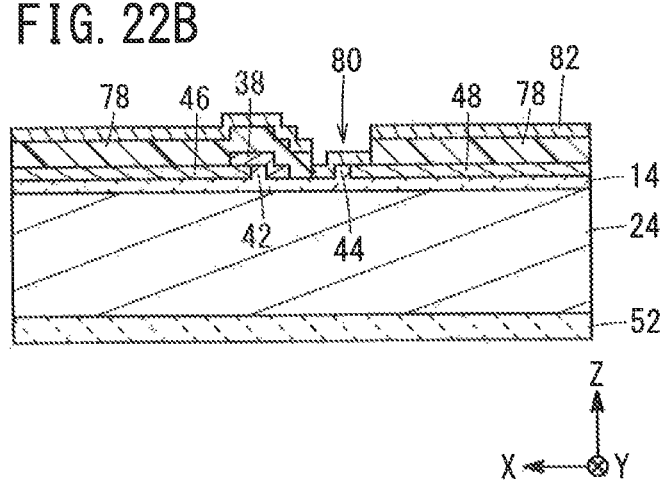
FIG. 22B is a cross-sectional view taken along the line XXIIB-XXIIB in FIG. 22A in the direction of the arrows.
Figure 23A:
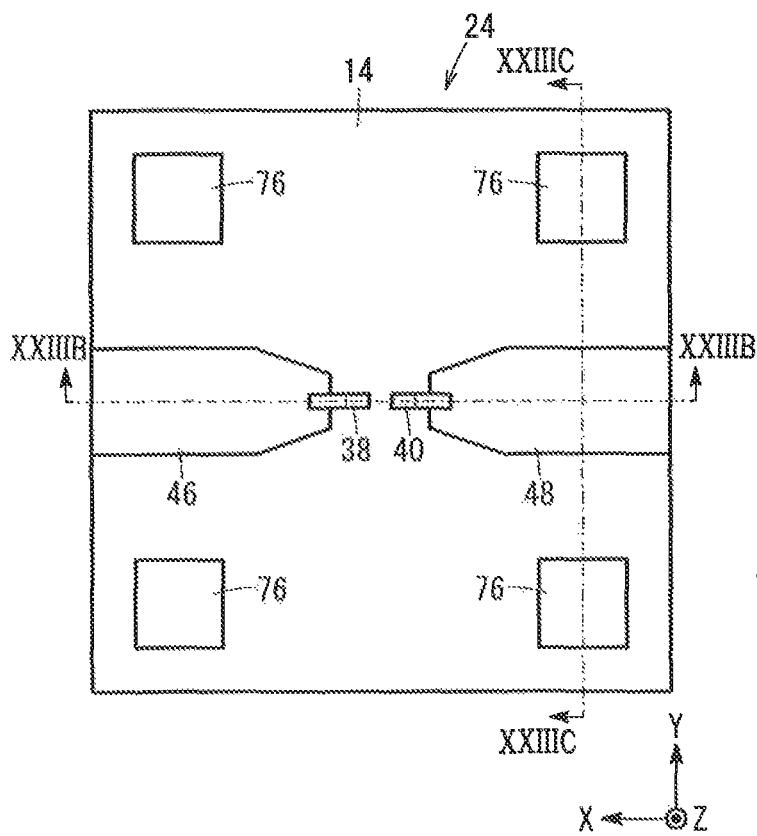
FIG. 23A is a plan view of a positive electrode active material obtained by removing the photoresist of FIG. 22A.
Figure 23C:
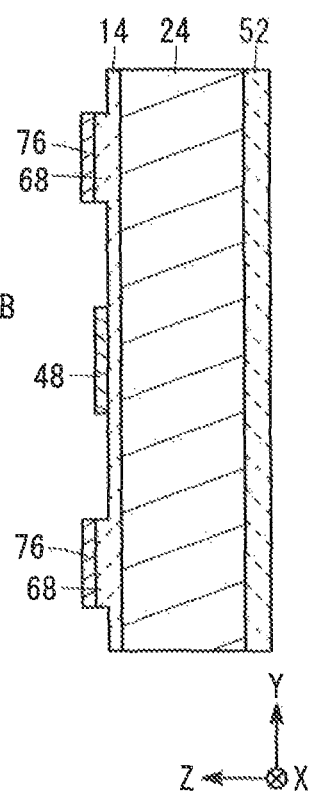
FIG. 23C is a cross-sectional view taken along the line XXIIIC-XXIIIC in FIG. 23A in the direction of the arrows.
Figure 23B:
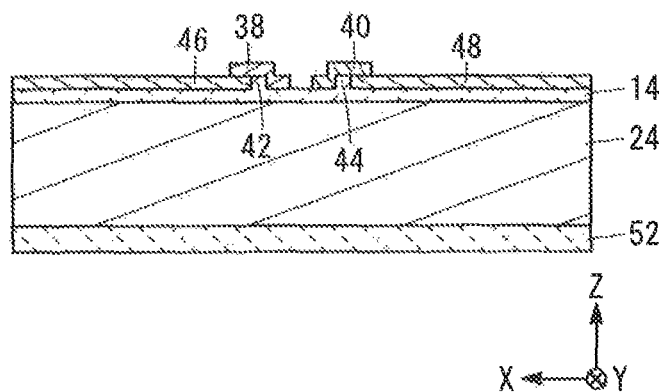
FIG. 23B is a cross-sectional view taken along the line XXIIIB-XXIIIB in FIG. 23A in the direction of the arrows.

As shown in FIGS. 22A to 22C, the one surface of the substrate 24 having the photoresist 78 and the positive electrode active material formation portion 80 is covered with a lithium cobaltate membrane by physical vapor deposition (PVD). The lithium cobaltate membrane is used as a precursor of the positive electrode active material 40 (a positive electrode active material precursor 82). As shown in FIGS. 23A to 23C, the photoresist 78 is lifted off to obtain the positive electrode active material 40.

Figure 24A:
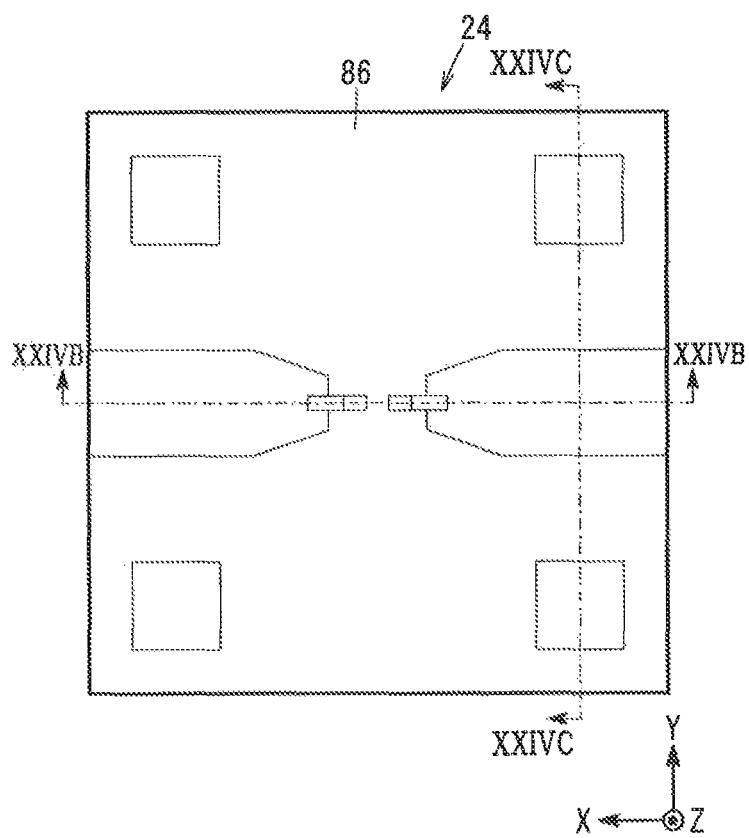
FIG. 24A is a plan view of a third spacer-shaped portion precursor formed on the one surface of the substrate of FIG. 23A.
Figure 24C:
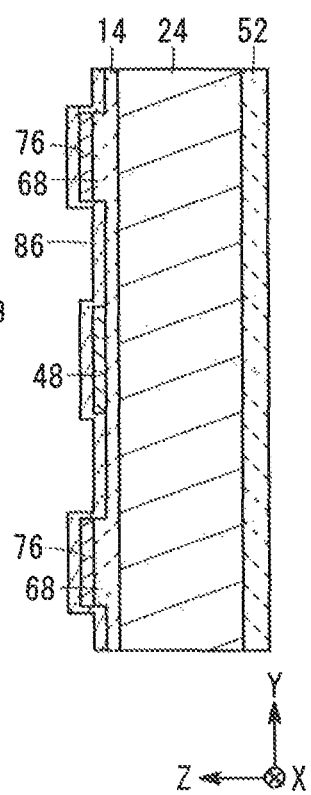
FIG. 24C is a cross-sectional view taken along the line XXIVC-XXIVC in FIG. 24A in the direction of the arrows.
Figure 24B:
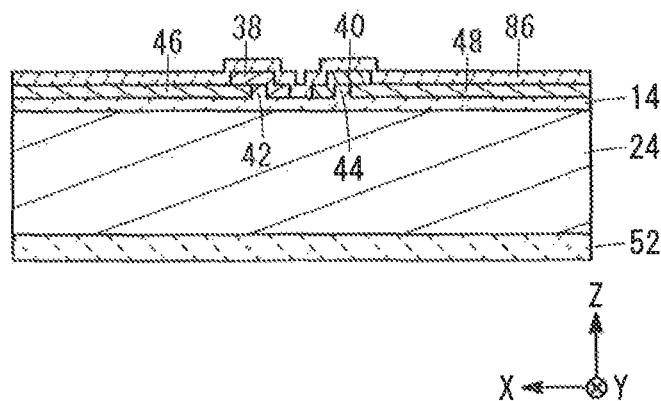
FIG. 24B is a cross-sectional view taken along the line XXIVB-XXIVB in FIG. 24A in the direction of the arrows.
Figure 25A:
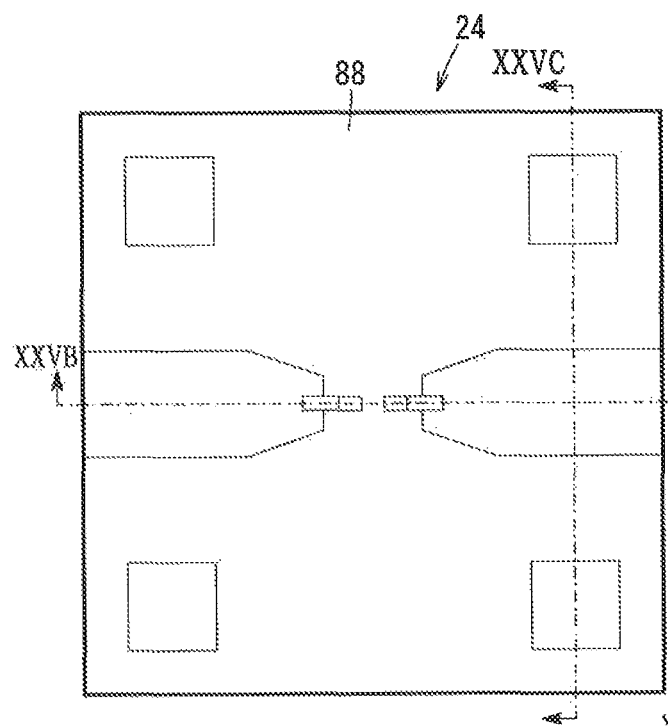
FIG. 25A is a plan view of a photoresist formed on the one surface of the substrate of FIG. 24A.
Figure 25C:
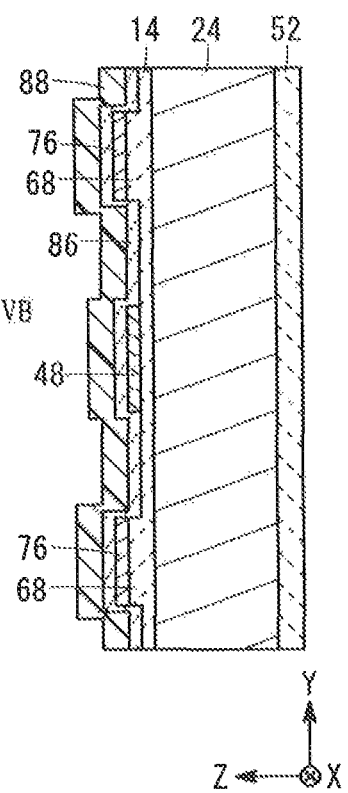
FIG. 25C is a cross-sectional view taken along the line XXVC-XXVC in FIG. 25A in the direction of the arrows.
Figure 25B:
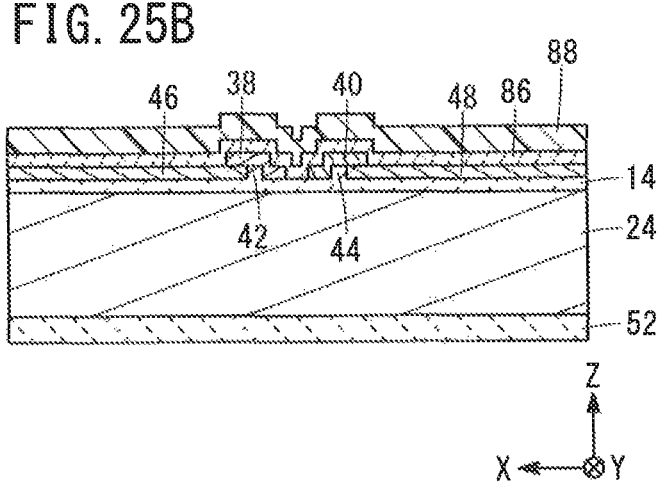
FIG. 25B is a cross-sectional view taken along the line XXVB-XXVB in FIG. 25A in the direction of the arrows.

As shown in FIGS. 24A to 24C, the one surface of the substrate 24 having the negative electrode active material 38, the positive electrode active material 40, the negative electrode collector 46, the positive electrode collector 48, the transmission membrane 14, and the second spacer-shaped portions 76 is covered with a silicon nitride membrane by chemical vapor deposition (CVD). The silicon nitride membrane is used as a precursor of third spacer-shaped portions 84 to be hereinafter described (third spacer-shaped portion precursor 86). As shown in FIGS. 25A to 25C, the one surface of the substrate 24 having the third spacer-shaped portion precursor 86 is covered with a photoresist 88.

Figure 26A:
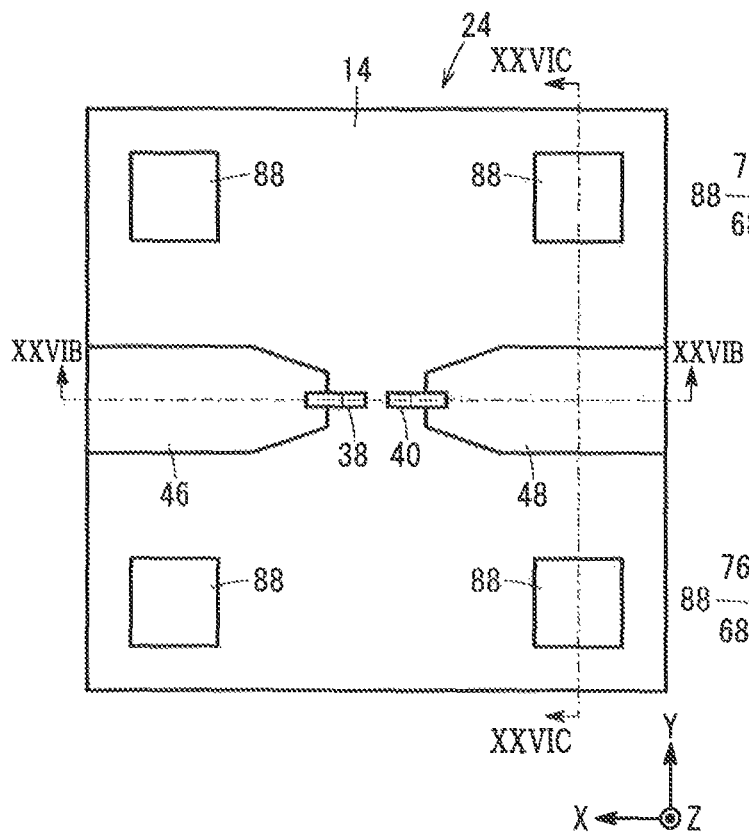
FIG. 26A is a plan view of photoresist residues remaining only on the second spacer-shaped portions formed by patterning the photoresist of FIG. 25A, the third spacer-shaped portion precursor being then removed in portions not covered with the photoresist.
Figure 26C:
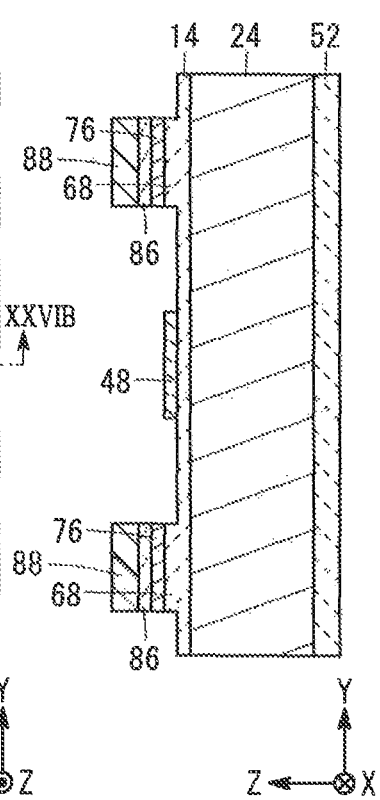
FIG. 26C is a cross-sectional view taken along the line XXVIC-XXVIC in FIG. 26A in the direction of the arrows.
Figure 26B:
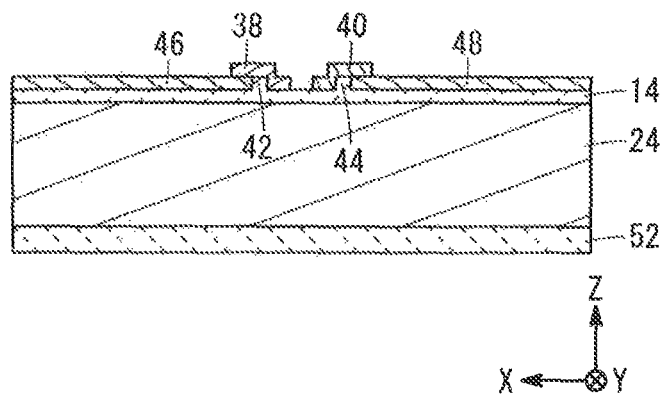
FIG. 26B is a cross-sectional view taken along the line XXVIB-XXVIB in FIG. 26A in the direction of the arrows.
Figure 27A:
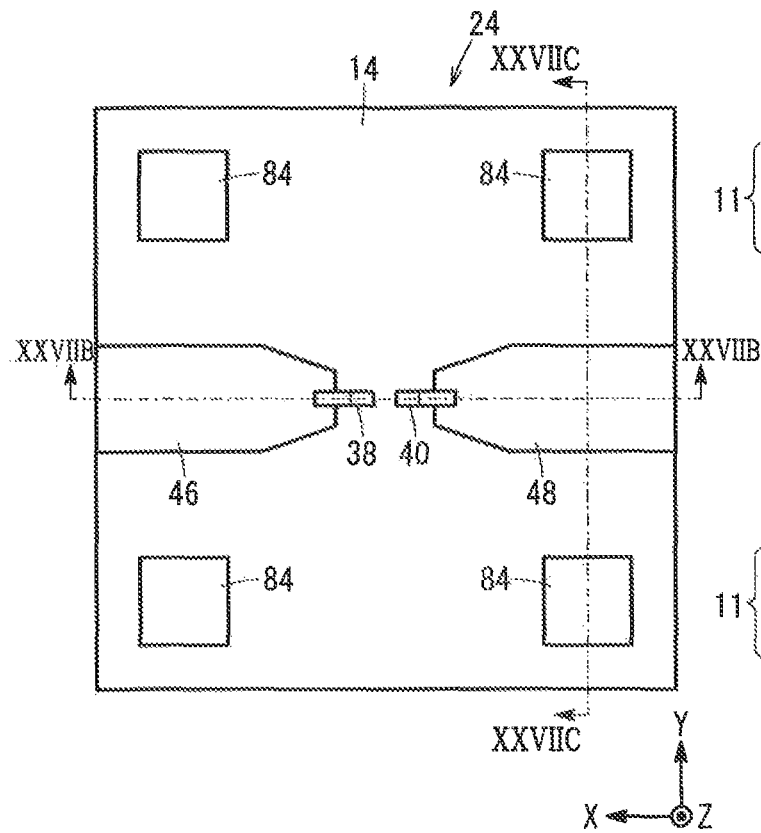
FIG. 27A is a plan view of third spacer-shaped portions obtained by removing the photoresist of FIG. 26A.
Figure 27C:
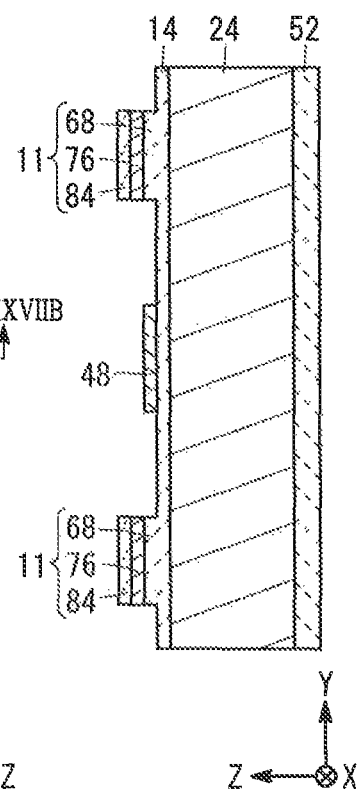
FIG. 27C is a cross-sectional view taken along the line XXVIIC-XXVIIC in FIG. 27A in the direction of the arrows.
Figure 27B:
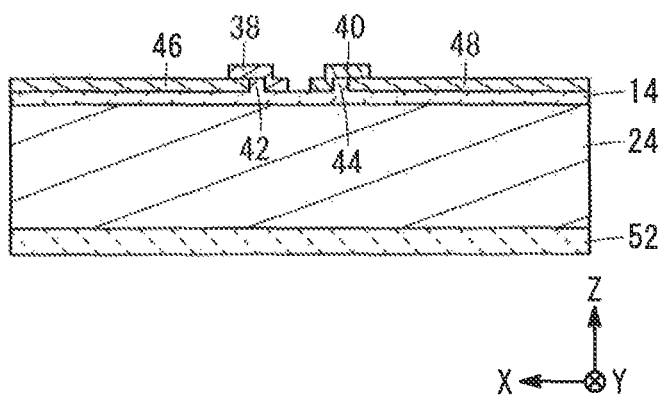
FIG. 27B is a cross-sectional view taken along the line XXVIIB-XXVIIB in FIG. 27A in the direction of the arrows.

As shown in FIGS. 26A to 26C, the photoresist 88 is patterned by a photolithography process, and a reactive ion etching process is carried out using the photoresist 88 as a mask. Thus, the photoresist 88 remains only on the third spacer-shaped portion precursor 86 on the second spacer-shaped portions 76, and the exposed portions of the third spacer-shaped portion precursor 86 around the residues of the photoresist 88 are removed by the reactive ion etching process. As shown in FIGS. 27A to 27C, the residues of the photoresist 88 residues are lifted off to obtain the third spacer-shaped portions 84 on the second spacer-shaped portions 76. Thus, the first spacer-shaped portions 68, the second spacer-shaped portions 76, and the third spacer-shaped portions 84 are stacked to form the spacers 11.

Figure 28A:
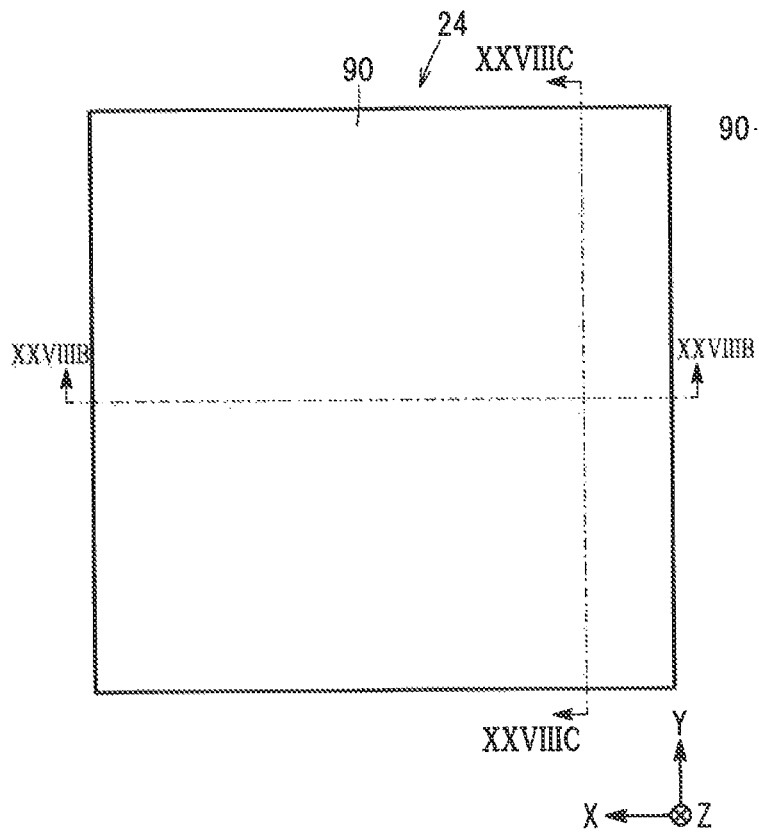
FIG. 28A is a plan view of a photoresist formed on the other surface of the substrate of FIG. 27A.
Figure 28C:
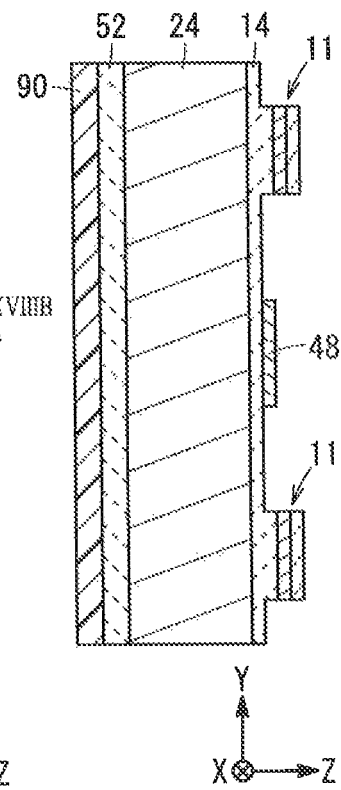
FIG. 28C is a cross-sectional view taken along the line XXVIIIC-XXVIIIC in FIG. 28A in the direction of the arrows.
Figure 28B:
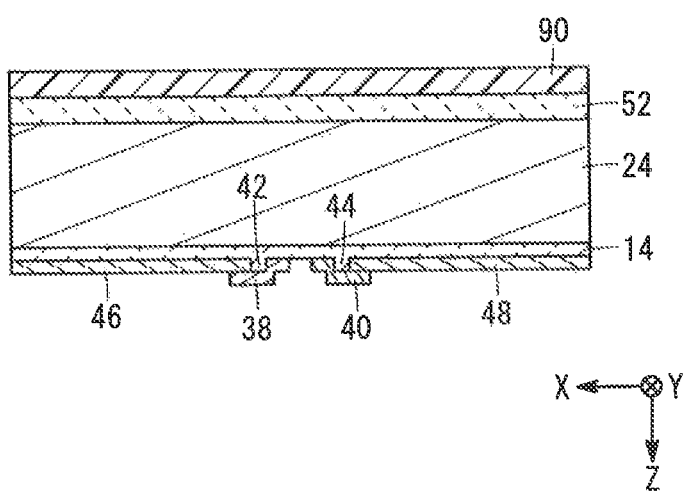
FIG. 28B is a cross-sectional view taken along the line XXVIIIB-XXVIIIB in FIG. 28A in the direction of the arrows.
Figure 29A:
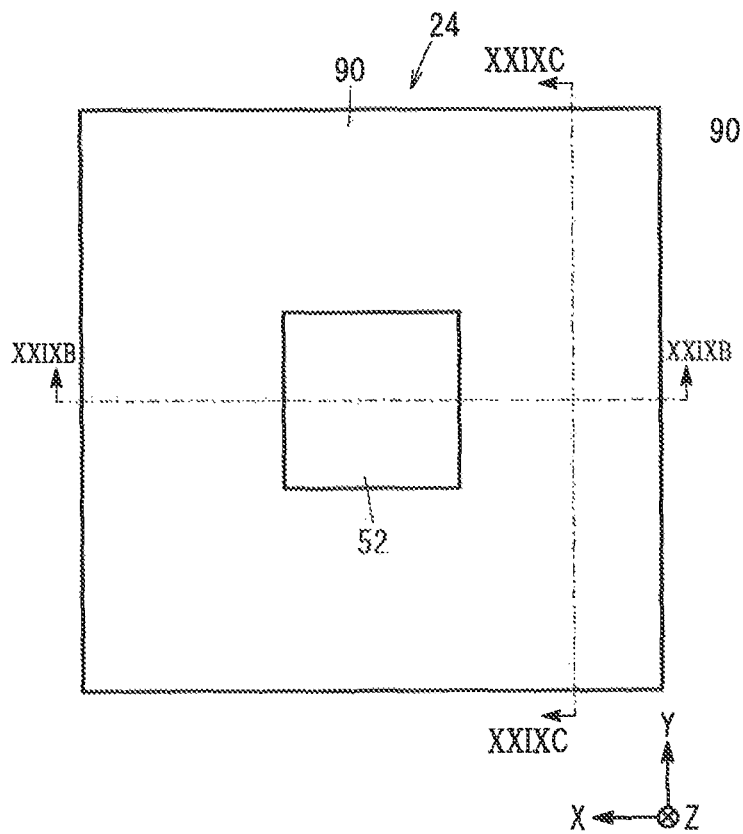
FIG. 29A is a plan view of an exposed portion in the covering membrane precursor, corresponding to a through-hole, formed by patterning the photoresist of FIG. 28A.
Figure 29C:
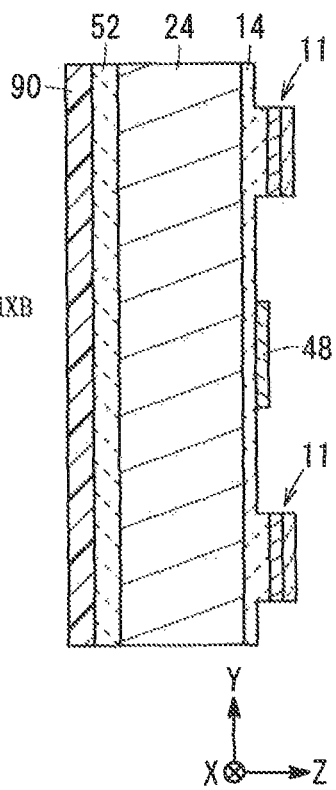
FIG. 29C is a cross-sectional view taken along the line XXIXC-XXIXC in FIG. 29A in the direction of the arrows.
Figure 29B:
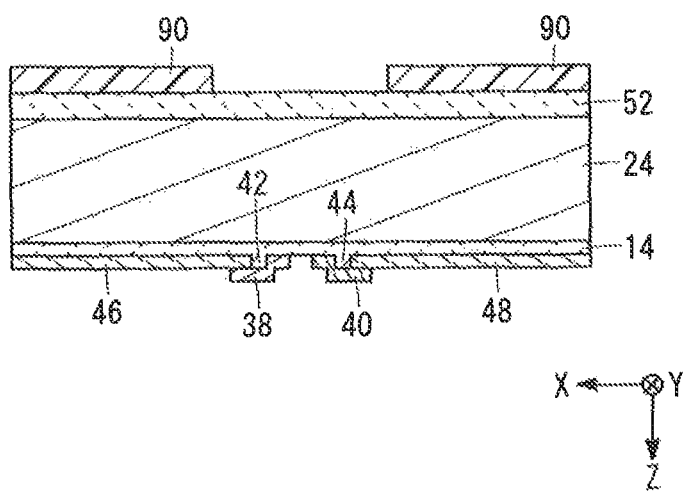
FIG. 29B is a cross-sectional view taken along the line XXIXB-XXIXB in FIG. 29A in the direction of the arrows.

As shown in FIGS. 28A to 28C, the other surface of the substrate 24 having the covering membrane precursor 52 is covered with a photoresist 90. As shown in FIGS. 29A to 29C, the photoresist 90 is removed by a photolithography process, such that the covering membrane precursor 52 is exposed in a portion corresponding to the through-hole 26 of the substrate 24.

Figure 31A:
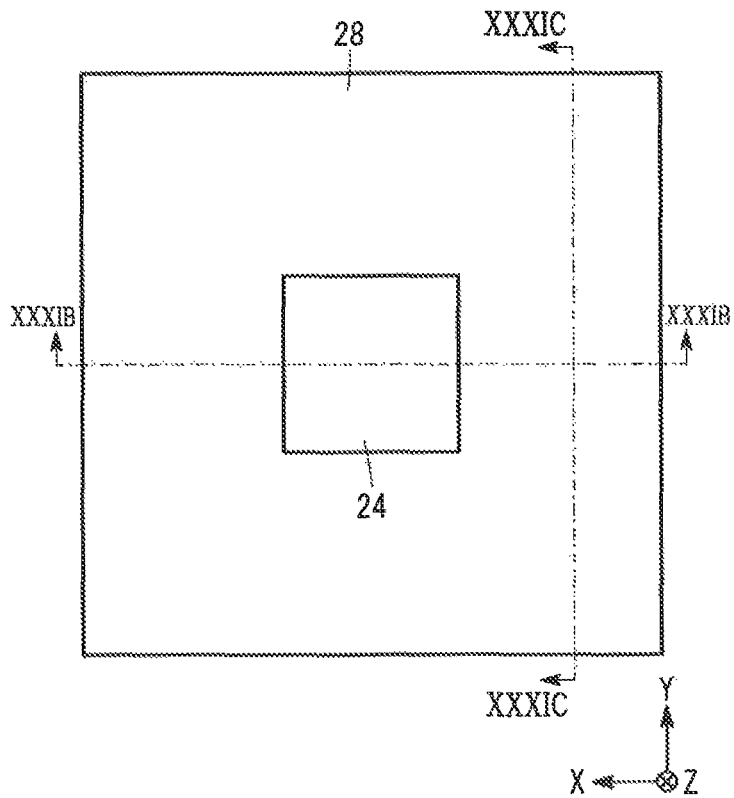
FIG. 31A is a plan view of a through-hole formation portion of the substrate exposed by removing the photoresist of FIG. 30A.
Figure 31C:
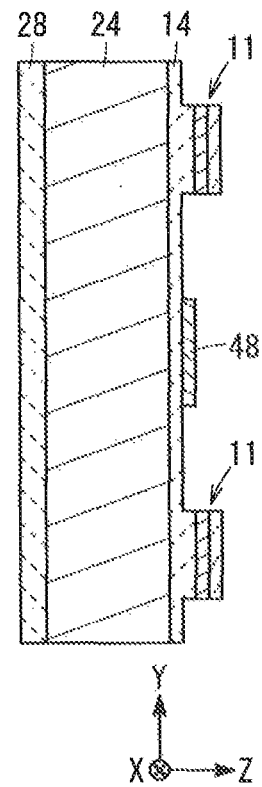
FIG. 31C is a cross-sectional view taken along the line XXXIC-XXXIC in FIG. 31A in the direction of the arrows.
Figure 31B:
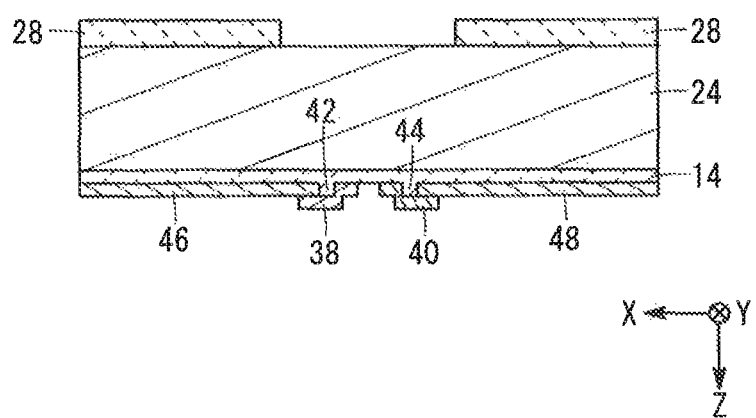
FIG. 31B is a cross-sectional view taken along the line XXXIB-XXXIB in FIG. 31A in the direction of the arrows.

As shown in FIGS. 30A to 30C, a reactive ion etching process is carried out using the photoresist 90 as a mask. Thus, in the covering membrane precursor 52, the portion exposed in the photoresist 90 is removed from the substrate 24. In other words, in the substrate 24, a portion corresponding to the through-hole 26 is exposed. As shown in FIGS. 31A to 31C, the photoresist 90 is lifted off to obtain the covering membrane 28, and then the one surface of the substrate 24 having the transmission membrane 14 is covered with an alkali-resistant surface protection layer (not shown).

Figure 32A:
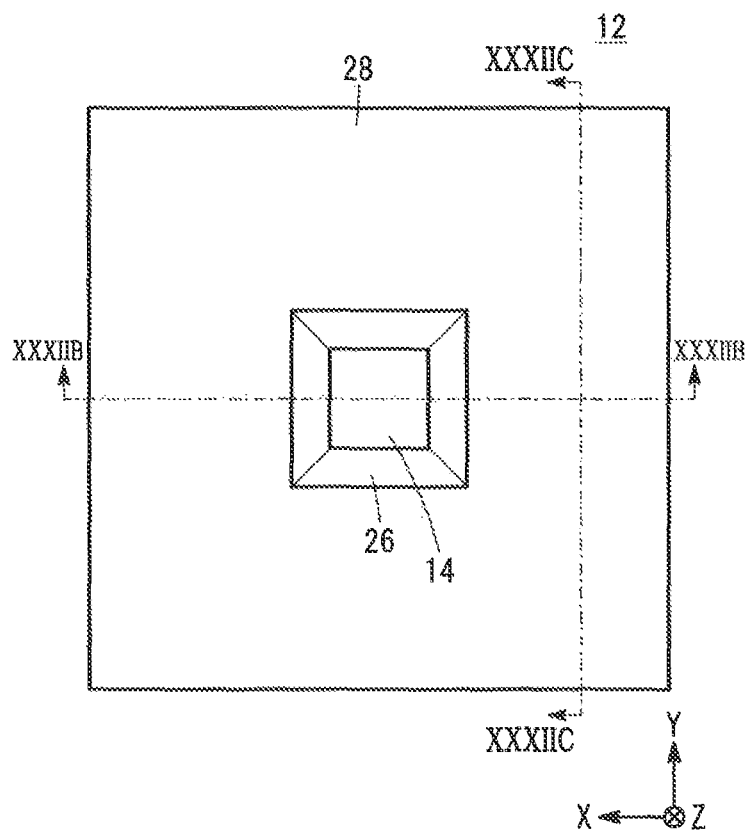
FIG. 32A is a plan view of a through-hole formed in the substrate of FIG. 31A.
Figure 32C:
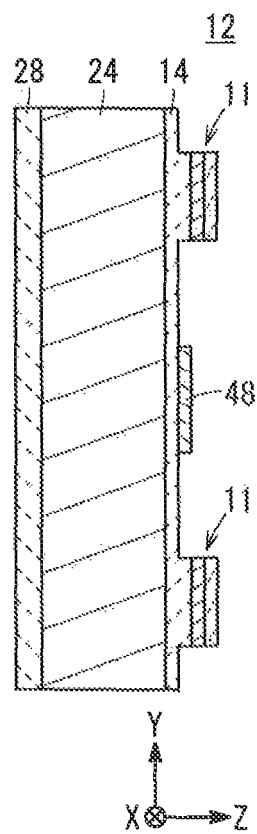
FIG. 32C is a cross-sectional view taken along the line XXXIIC-XXXIIC in FIG. 32A in the direction of the arrows.
Figure 32B:
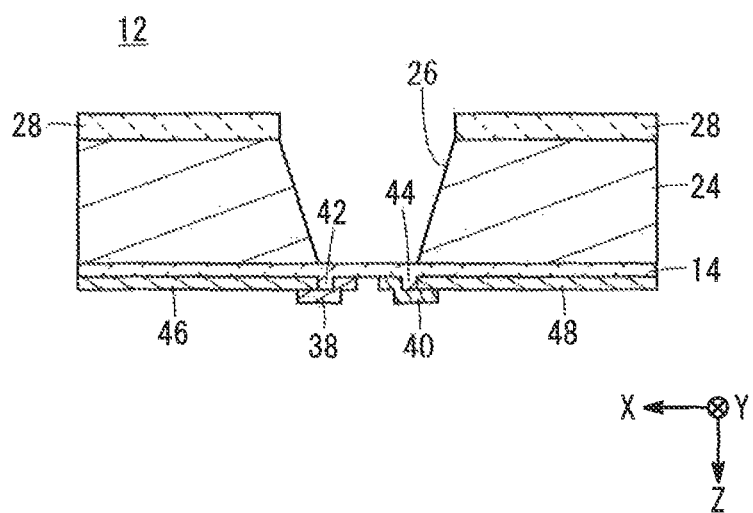
FIG. 32B is a cross-sectional view taken along the line XXXIIB-XXXIIB in FIG. 32A in the direction of the arrows.

As shown in FIGS. 32A to 32C, the other surface of the substrate 24 is subjected to a penetration etching process using the photoresist 90 as a mask to form the through-hole 26. In this process, the one surface of the substrate 24 is protected by the alkali-resistant surface protection layer. Then, a reactive ion etching process is carried out to remove the alkali-resistant surface protection layer, whereby the first holder 12 is obtained. The first holder 12 contains the substrate 24 having the through-hole 26, and the transmission membrane 14 is disposed on the one surface of the substrate 24, such that one end of the through-hole 26 is covered with the transmission membrane 14.

In the preparation of the second holder 16, both surfaces of the substrate 30 are polished in the same manner as the substrate 24 to be covered with the transmission membrane precursor 50 and the covering membrane precursor 52. The one surface of the substrate 30 is covered with a silicon nitride membrane used as the transmission membrane 18, and the other surface is covered with a silicon nitride membrane used as a covering membrane precursor 52. Then, the covering membrane 34 and the through-hole 32 are formed on the substrate 30 in the same manner as the processing of the other surface of the substrate 24. Thus, the through-hole 32 is formed in the substrate 30, and the transmission membrane 18 is disposed on the one surface of the substrate 30, such that one end of the through-hole 32 is covered with the transmission membrane 18, whereby the second holder 16 is prepared.

After the first holder 12 and the second holder 16 are prepared as described above, the electrolytic solution is applied to the one surface of the first holder 12 in such a manner that the negative electrode active material 38 and the positive electrode active material 40 are each brought into contact with the electrolytic solution. The second holder 16 is stacked on the first holder 12 as described above. Thus, the first holder 12 and the second holder 16 are stacked to form the overlapping portion 20, and the through-holes 26, 32 face each other across the transmission membranes 14, 18 to form the observation window 36. In this process, in each end of the first holder 12, the portion having the width L protrudes from the overlapping portion 20.

Then, the sealant 22 is formed around the overlapping portion 20, whereby the inner space of the overlapping portion 20 filled with the electrolytic solution is sealed. In the process of forming the sealant 22, the metal wires are fixed and electrically connected to the exposed portions of the negative electrode collector 46 and the positive electrode collector 48, protruding from the overlapping portion 20. The analytical cell 10 is produced in this manner. Thus, the analytical cell 10 can be produced more easily at lower cost by the known semiconductor process than by ion beam deposition methods, etc.

As described above, the negative electrode active material 38, the positive electrode active material 40, the transmission bodies 42, 44, the negative electrode collector 46, and the positive electrode collector 48 are formed on the transmission membrane 14 in the first holder 12. Therefore, in the production of the analytical cell 10, the steps of forming the components can be carried out using only the first holder 12. Consequently, the analytical cell 10 can be easily and efficiently obtained by a simple production process.

Second Embodiment

Figure 34:
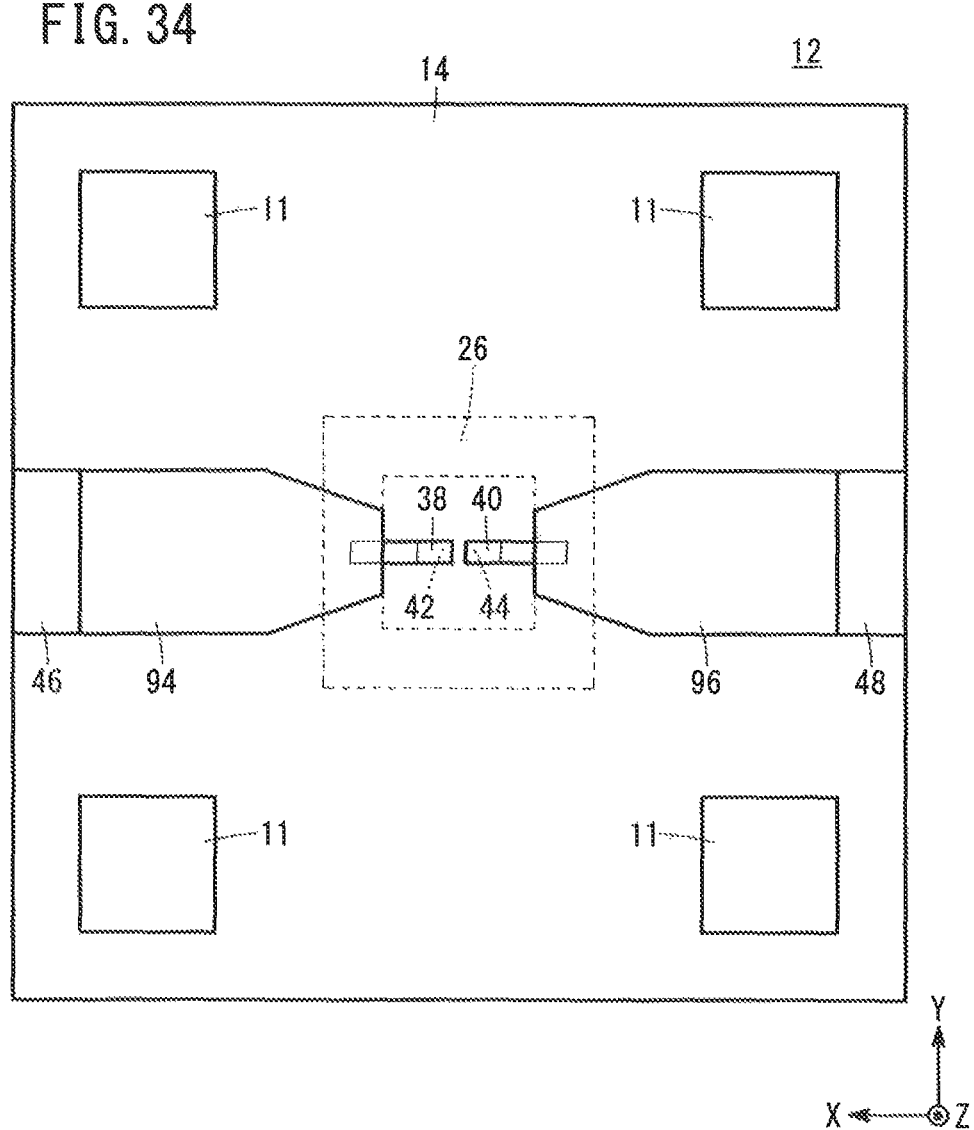
FIG. 34 is a plan view of a transmission membrane side of a first holder in the analytical cell of FIG. 33.

An analytical cell 92 according to a second embodiment will be described below with reference to FIGS. 33 and 34. FIG. 33 is a cross-sectional view of the analytical cell 92 taken in the same direction as FIG. 2. FIG. 34 is a plan view of a transmission membrane 14 side of the first holder 12 in the analytical cell 92. The components in FIGS. 33 and 34, equal or similar in functions and effects to those in FIGS. 1 to 32C, are denoted by the same reference numerals, and detailed explanations thereof are omitted.

The analytical cell 92 contains isolation membranes 94, 96 in addition to the above-described components of the analytical cell 10. Specifically, one surface of the negative electrode collector 46 is in contact with the transmission membrane 14, and the other surface is covered with the isolation membrane 94 inside the overlapping portion 20. Similarly, one surface of the positive electrode collector 48 is in contact with the transmission membrane 14, and the other surface is covered with the isolation membrane 96 inside the overlapping portion 20. For example, the isolation membranes 94, 96 each contain an electrically insulating substance such as silicon nitride, and act to avoid the contact of the electrolytic solution with the negative electrode collector 46 and the positive electrode collector 48 inside the overlapping portion 20, respectively.

Thus, in the overlapping portion 20 of the analytical cell 92, the negative electrode active material 38 and the positive electrode active material 40 are in contact with the electrolytic solution, while the negative electrode collector 46 and the positive electrode collector 48 are not in contact with the electrolytic solution, as described above. Therefore, side reactions, different from the electrode reactions as the observation subject, can be suppressed in the negative electrode active material 38 and the positive electrode active material 40. Consequently, the electrode reactions of the negative electrode active material 38 and the positive electrode active material 40 can be more accurately analyzed.

For example, the analytical cell 92 may be produced in the same manner as the above analytical cell 10 except for performing the following photolithography process instead of the photolithography process for the photoresist 88 shown in FIGS. 26A to 26C. In this case, the photoresist 88 remains also on portions to be covered with the isolation membranes 94, 96, whereby the isolation membranes 94, 96 are obtained from the third spacer-shaped portion precursor 86. As a result, in the final product of the analytical cell 92, the negative electrode collector 46 and the positive electrode collector 48 are covered with the isolation membranes 94, 96 inside the overlapping portion 20.

Third Embodiment

Figure 35:
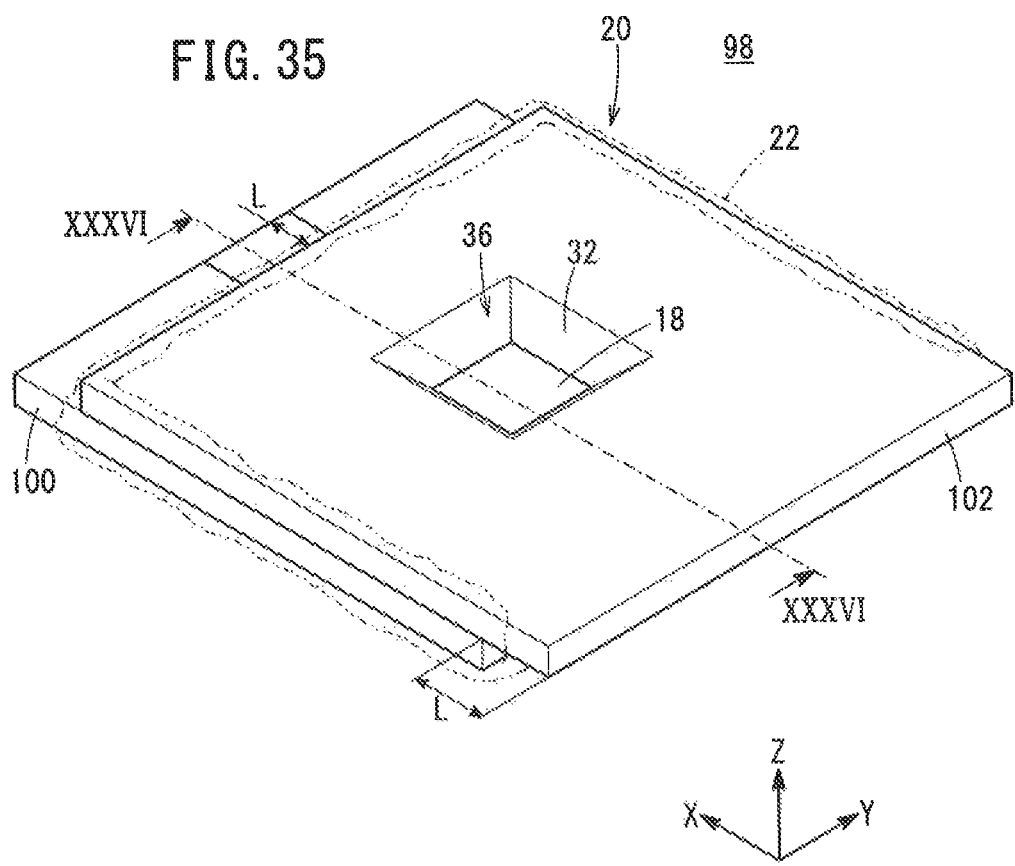
FIG. 35 is an overall schematic perspective view of an analytical cell according to a third embodiment of the present invention.
Figure 36:
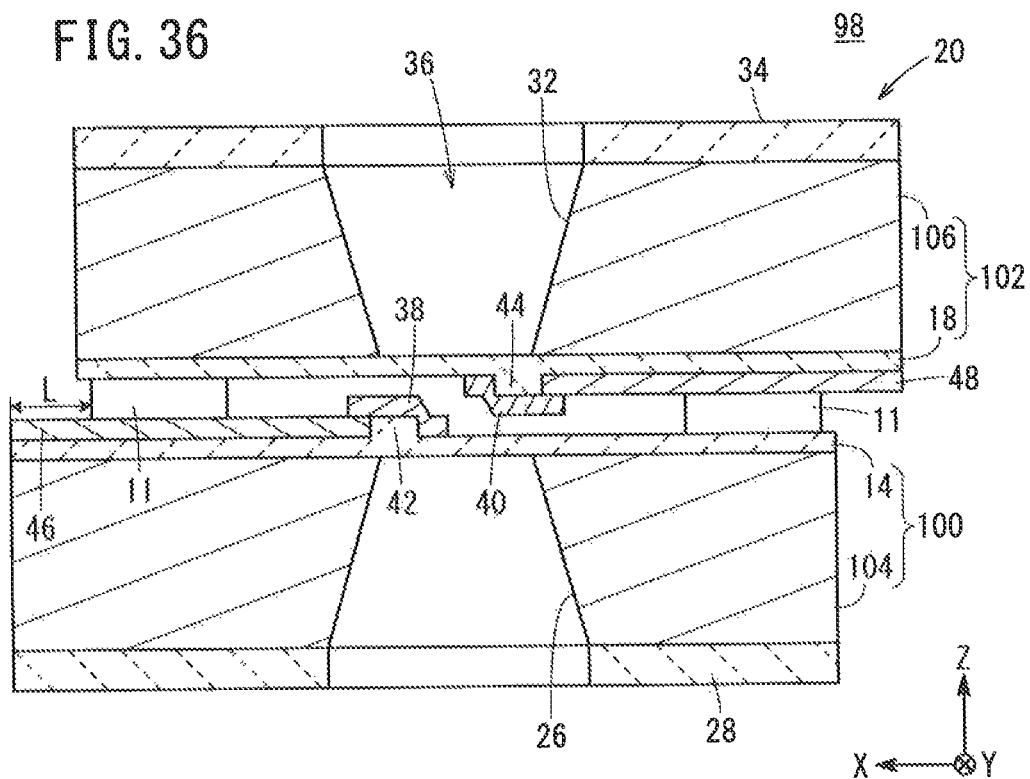
FIG. 36 is a cross-sectional view of the analytical cell of FIG. 35 taken along the line XXXVI-XXXVI in the direction of the arrows.
Figure 37:
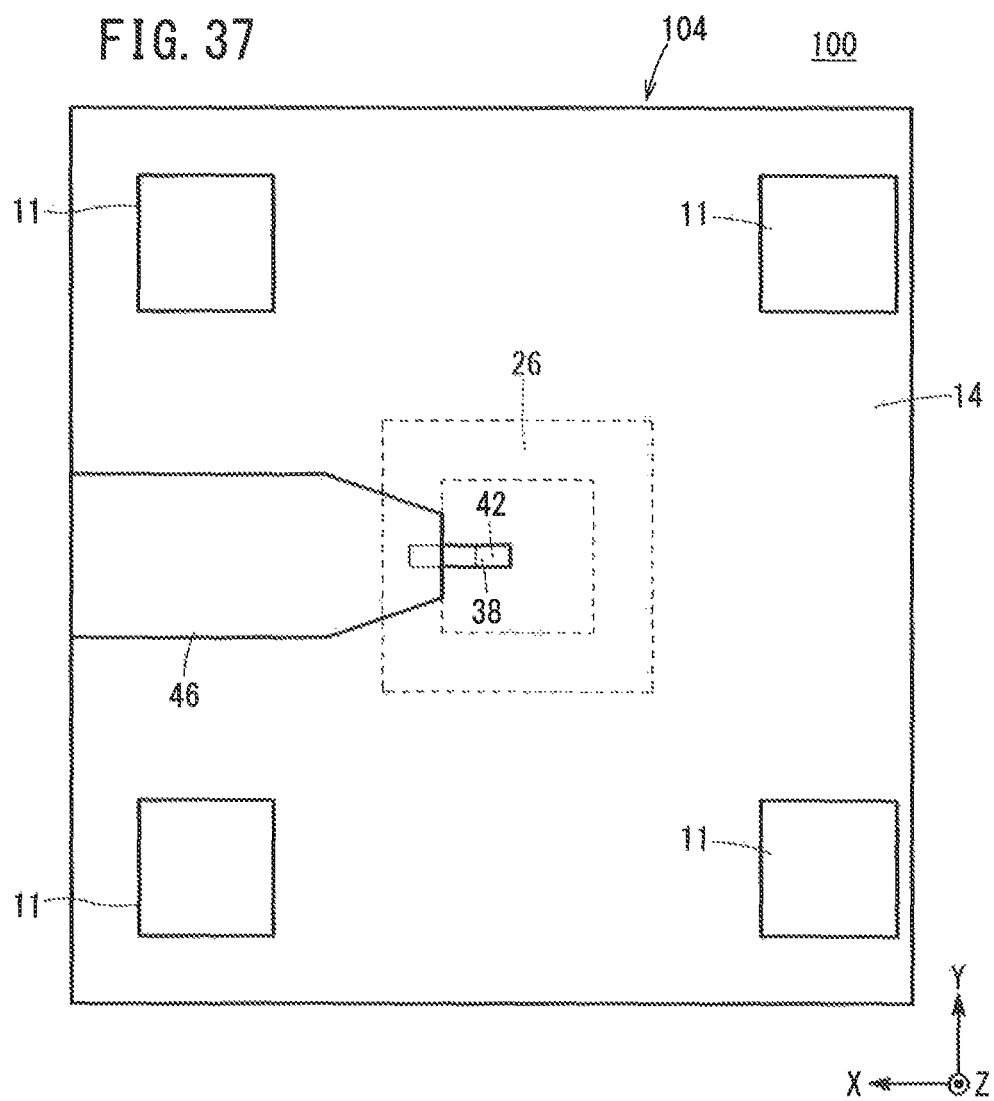
FIG. 37 is a plan view of a transmission membrane side of a first holder in the analytical cell of FIG. 35.
Figure 38:
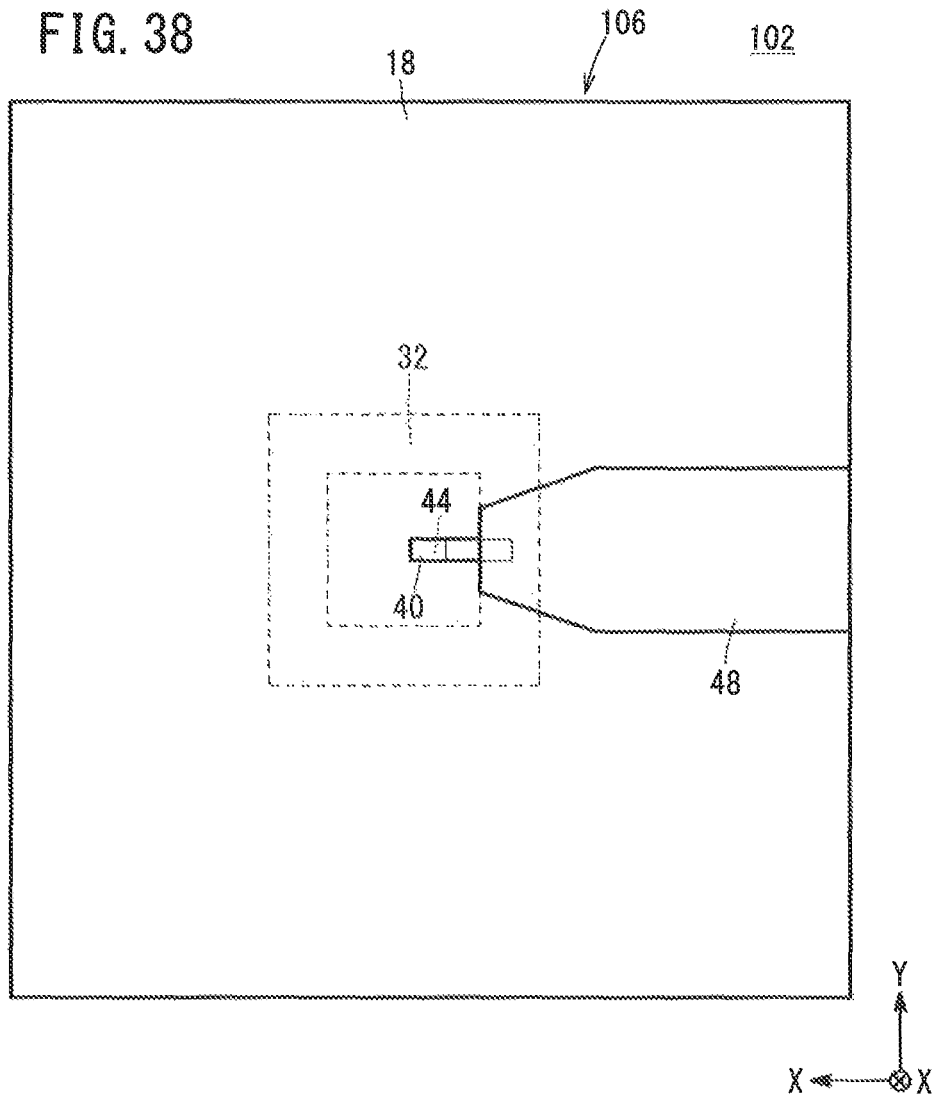
FIG. 38 is a plan view of a transmission membrane side of a second holder in the analytical cell of FIG. 35.

An analytical cell 98 according to a third embodiment will be described below with reference to FIGS. 35 to 38. FIG. 35 is an overall schematic perspective view of the analytical cell 98. FIG. 36 is a cross-sectional view of the analytical cell 98 of FIG. 35 taken along the line XXXVI-XXXVI in the direction of the arrows. FIG. 37 is a plan view of a transmission membrane 14 side of a first holder 100 in the analytical cell 98. FIG. 38 is a plan view of a transmission membrane 18 side of a second holder 102 in the analytical cell 98. The components in FIGS. 35 to 38, equal or similar in functions and effects to those in FIGS. 1 to 34, are denoted by the same reference numerals, and detailed explanations thereof are omitted.

The analytical cell 98 contains the first holder 100 and the second holder 102 instead of the first holder 12 and the second holder 16 in the analytical cell 10. The first holder 100 contains a substrate 104 instead of the substrate 24, and the second holder 102 contains a substrate 106 instead of the substrate 30.

The substrate 104 is different from the substrate 24 in that the through-hole 26 is slightly shifted from the center of the substrate 104 toward one end in the width direction. The substrate 106 is different from the substrate 30 in that the substrate 106 has approximately the same shape as the substrate 104 in the first holder 100.

As described above, the first holder 100 and the second holder 102 are stacked to form the overlapping portion 20 in such a manner that the through-holes 26, 32 in the substrates 104, 106 face each other across the transmission membranes 14, 18. Therefore, in the analytical cell 98, one end of the first holder 100 and the other end of the second holder 102 protrude from the overlapping portion 20 in the width direction respectively to form exposed portions having the width L.

Furthermore, in the analytical cell 98, one surface of the negative electrode active material 38 and one surface of the negative electrode collector 46 are in contact with the transmission membrane 14 in the first holder 100, and one surface of the positive electrode active material 40 and one surface of the positive electrode collector 48 are in contact with the transmission membrane 18 in the second holder 102. Thus, the negative electrode active material 38, the transmission body 42, and the negative electrode collector 46 are formed on the first holder 100, and the positive electrode active material 40, the transmission body 44, and the positive electrode collector 48 are formed on the second holder 102. In this embodiment, the negative electrode active material 38 and the positive electrode active material 40 are formed on different holders (the first holder 100 and the second holder 102), whereby the negative electrode active material 38 and the positive electrode active material 40 are not arranged excessively close to each other and are not in contact with each other.

Consequently, the analytical cell 98 has the same advantageous effects as the analytical cell 10, and, in addition, is capable of effectively preventing short-circuit of the negative electrode active material 38 and the positive electrode active material 40 even when they are arranged in a small space.

For example, the analytical cell 98 may be produced in the same manner as the above analytical cell 10 except for using the substrate 106 in the second holder 102 in the steps of forming the positive electrode active material 40, the transmission body 44, and the positive electrode collector 48. As a result, in the final product of the analytical cell 98, the negative electrode active material 38 and the positive electrode active material 40 are formed on the different holders (the first holder 100 and the second holder 102).

Figure 39:
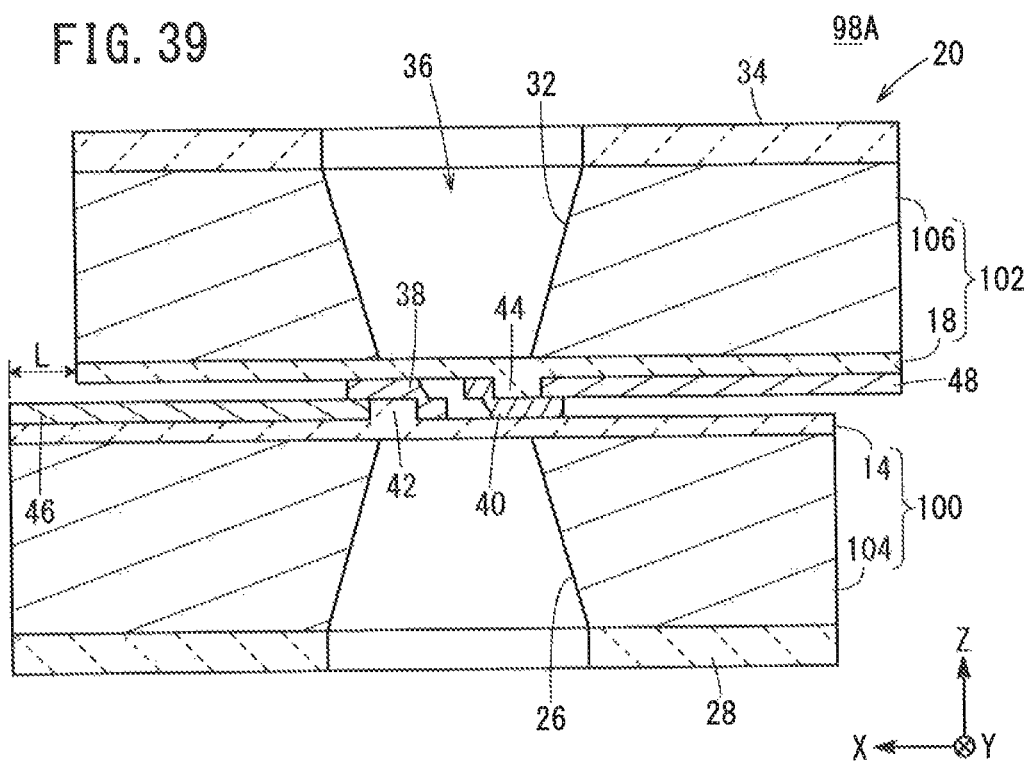
FIG. 39 is a cross-sectional view of an analytical cell according to a modification example of FIG. 35 taken in the same direction as FIG. 36.

It is not necessary to form the spacers 11 in the analytical cell 98 in a case where the desired space can be formed in the overlapping portion 20 without the spacers 11 as in an analytical cell 98A shown in FIG. 39. The components in FIG. 39, equal or similar in functions and effects to those in FIGS. 1 to 38, are denoted by the same reference numerals, and detailed explanations thereof are omitted. The analytical cell 98A has the same structure as the analytical cell 98 except that the spacers 11 are not formed.

Fourth Embodiment

An analytical cell 108 according to a fourth embodiment will be described below with reference to FIG. 40. FIG. 40 is a cross-sectional view of the analytical cell 108 taken in the same direction as FIGS. 2 and 36. The components in FIG. 40, equal or similar in functions and effects to those in FIGS. 1 to 39, are denoted by the same reference numerals, and detailed explanations thereof are omitted.

The analytical cell 108 contains the isolation membranes 94, 96 as in the second embodiment in addition to the above-described components of the analytical cell 98. Thus, in the overlapping portion 20, the contact of the electrolytic solution with the negative electrode collector 46 and the positive electrode collector 48 can be avoided by the isolation membranes 94, 96. Therefore, side reactions, different from the electrode reactions of the observation subject, can be suppressed in the negative electrode collector 46 and the positive electrode collector 48. Consequently, the analytical cell 108 has the same advantageous effects as the analytical cells 10, 98, and, in addition, is capable of more highly accurately analyzing the electrode reactions and the like of the negative electrode active material 38 and the positive electrode active material 40.

For example, the analytical cell 108 may be produced in the same manner as the above analytical cell 92 except for forming the isolation membrane 96 on the substrate 106 in the second holder 102. As a result, in the final product of the analytical cell 108, the negative electrode collector 46 and the positive electrode collector 48 are covered with the isolation membranes 94, 96 in the overlapping portion 20, and the combination of the negative electrode collector 46 and the isolation membrane 94 and the combination of the positive electrode collector 48 and the isolation membrane 96 are formed on the different holders (the first holder 100 and the second holder 102).

The present invention is not limited to the above embodiments, and various changes and modifications may be made therein without departing from the scope of the invention.

For example, in the analytical cells 10, 92, the transmission body 42, 44 is formed between the transmission membrane 14 and each of the negative electrode active material 38 and the positive electrode active material 40. However, the present invention is not limited thereto, and only one transmission body 42, 44 may be formed between the transmission membrane 14 and one of the negative electrode active material 38 and the positive electrode active material 40. Similarly, in the analytical cells 98, 108, at least one of the transmission bodies 42, 44 may be formed between the transmission membrane 14 and the negative electrode active material 38 or between the transmission membrane 18 and the positive electrode active material 40.

In the analytical cells 92, 108, the negative electrode collector 46 and the positive electrode collector 48 have the isolation membranes 94, 96 respectively. However, the present invention is not limited thereto, and only one of the negative electrode collector 46 and the positive electrode collector 48 may have the isolation membrane 94 or the isolation membrane 96.

In a case where the analytical cell 10 or the like of the above embodiment is not the lithium-ion secondary cell but the nickel-hydrogen cell, for example, a negative electrode of nickel hydroxide, a positive electrode of a hydrogen storing alloy, and an electrolytic solution of an aqueous potassium hydroxide solution KOH(aq) may be used. In a case where the analytical cell 10 is the alkaline-manganese cell, for example, a negative electrode of manganese dioxide/graphite, a positive electrode of zinc, and an electrolytic solution of KOH(aq) may be used.

The analytical cell 10 and the like can be used in an analysis not only in the TEM but also in every analytical equipment using an electron beam.

What is claimed is:
1. An analytical cell, through which an electron beam is transmitted to perform an analysis, comprising a first holder and a second holder stacked with an electrolytic solution interposed therebetween, wherein
- the first holder and the second holder each contain a substrate including a through-hole and a transmission membrane having an electron beam permeability, the through-hole extends in a thickness direction of the substrate, the transmission membrane is disposed on one surface of the substrate, such that one end of the through-hole is covered with the transmission membrane,
- the first holder and the second holder are stacked to form an overlapping portion in such a manner that the surfaces of the substrates with the transmission membranes formed thereon face each other,
- in the overlapping portion, an inner space containing the electrolytic solution is sealed, and the through-holes face each other across the transmission membranes to form an observation window, through which an electron beam is transmitted,
- a negative electrode active material and a positive electrode active material are arranged at a distance from each other and respectively in contact with the electrolytic solution between the transmission membranes in the observation window, and
- a transmission body containing an electron beam permeable solid is formed between at least one of the negative electrode active material and the positive electrode active material and the transmission membrane in the observation window.

2. The analytical cell according to claim 1, wherein the negative electrode active material, the positive electrode active material, and the transmission body are formed on the first holder.

3. The analytical cell according to claim 1, wherein
- the negative electrode active material is formed on the first holder,
- the positive electrode active material is formed on the second holder, and
- the transmission body is formed on at least one of the first holder and the second holder.

4. The analytical cell according to claim 1, further comprising a negative electrode collector and a positive electrode collector, wherein
- the negative electrode collector and the positive electrode collector are electrically connected to the negative electrode active material and the positive electrode active material respectively in the overlapping portion,
- the negative electrode collector and the positive electrode collector each extend from inside of the overlapping portion and are exposed to outside, and
- at least one of the negative electrode collector and the positive electrode collector has an isolation membrane configured to avoid contact with the electrolytic solution in the overlapping portion.

* * * * *